(12) United States Patent
Gruis et al.

(10) Patent No.: US 9,163,233 B2
(45) Date of Patent: *Oct. 20, 2015

(54) COMPOSITIONS AND METHODS FOR MODULATING EXPRESSION OF GENE PRODUCTS

(71) Applicant: Pioneer Hi-Bred International, Inc., Johnston, IA (US)

(72) Inventors: Darren B. Gruis, Baxter, IA (US); Craig Hastings, Perry, IA (US)

(73) Assignee: PIONEER HI-BRED INTERNATIONAL, INC., Johnston, IA (US)

( * ) Notice: Subject to any disclaimer, the term of this patent is extended or adjusted under 35 U.S.C. 154(b) by 187 days.

This patent is subject to a terminal disclaimer.

(21) Appl. No.: 13/775,772

(22) Filed: Feb. 25, 2013

(65) Prior Publication Data

US 2013/0198905 A1 Aug. 1, 2013

Related U.S. Application Data

(63) Continuation of application No. 12/569,213, filed on Sep. 29, 2009, now Pat. No. 8,404,929, which is a continuation of application No. 11/513,330, filed on Aug. 29, 2006, now abandoned.

(60) Provisional application No. 60/712,354, filed on Aug. 30, 2005.

(51) Int. Cl.
  *C12N 15/82* (2006.01)
  *C12N 15/87* (2006.01)
  *C12N 15/113* (2010.01)

(52) U.S. Cl.
  CPC .......... *C12N 15/113* (2013.01); *C12N 15/8216* (2013.01); *C12N 15/8218* (2013.01); *C12N 15/8222* (2013.01); *C12N 15/8234* (2013.01); *C12N 15/8235* (2013.01); *C12N 15/8245* (2013.01); *C12N 15/8246* (2013.01)

(58) Field of Classification Search
  CPC ............. C12N 15/113; C12N 15/8216; C12N 15/8218; C12N 15/8222; C12N 15/8234; C12N 15/8235; C12N 15/8245; C12N 15/8246
  See application file for complete search history.

(56) References Cited

U.S. PATENT DOCUMENTS

| | | | |
|---|---|---|---|
| 5,689,054 A | 11/1997 | Raboy | |
| 6,194,638 B1 * | 2/2001 | Dhugga et al. | 800/284 |
| 6,326,193 B1 | 12/2001 | Liu et al. | |
| 7,009,087 B1 | 3/2006 | Sewalt et al. | |
| 8,404,929 B2 * | 3/2013 | Gruis et al. | 800/286 |
| 2002/0182223 A1 | 12/2002 | LaCount et al. | |
| 2003/0204870 A1 * | 10/2003 | Allen et al. | 800/281 |
| 2004/0147475 A1 | 7/2004 | Li et al. | |
| 2006/0041957 A1 | 2/2006 | McGonigle et al. | |
| 2006/0150286 A1 | 7/2006 | Huang et al. | |
| 2006/0156428 A1 * | 7/2006 | Rommens et al. | 800/278 |
| 2006/0242736 A1 | 10/2006 | Huang et al. | |
| 2006/0247202 A1 | 11/2006 | Glassman et al. | |
| 2007/0089200 A1 | 4/2007 | Bao et al. | |
| 2007/0192896 A1 | 8/2007 | Malvar et al. | |

FOREIGN PATENT DOCUMENTS

WO  WO 2005/121347  12/2005

OTHER PUBLICATIONS

Brummelkamp, T.R., et al., "A System for Stable Expression of Short Interfering RNAs in Mammalian Cells," *Science*, 2002, pp. 550-553, vol. 296.
Dykxhoorn, D.M., et al., Killing the Messenger: Short RNAs that Silence Gene Expression, *Molecular Cell Biology*, 2003, pp. 457-467, vol. 4.
Johnson, C.S., et al., "Transparent TESTA GLABRA2, a Trichome and Seed Coat Development Gene of Arabidopsis, Encodes a WRKY Transcription Factor," *The Plant Cell*, 2002, pp, 1359-1375, vol. 4.
Lee, N.S., et al., "Expression of Small Interfacing RNAs Targeted Against HIV-1 *rev* Transcripts in Human Cells," *Nature Biotechnology*, 2002, pp. 500-505, vol. 19.
Lin, S-L., et al., "A Novel RNA Splicing-Mediated Gene Silencing Mechanism Potential for Genome Evolution," *Biochem, Biophys. Res. Commun.*, 2003, pp. 754-760, vol. 310(3).
Paddison, P.J., et al., "Short Hairpin RNAs (shRNAs) Induce Sequence-Specific Silencing in Mammalian Cells," *Genes & Development*, 2002, pp. 948-958, vol. 16.
Shi, J. et al., "The Maize Low-Phytic Acid Mutant *lpa2* Is Caused by Mutation in an Inositol Phosphate Kinase Gene," *Plant Physiology*, 2003, pp. 507-515, vol. 131.
Waterhouse, P.M., and C.A. Helliwell, "Exploring Plant Genomes by RNA-Induced Gene Silencing," *Nature Reviews*, 2003, pp. 29-38, vol. 4.
Yu, J-Y, et al., RNA Interference by Expression of Short-Interfering RNAs and Hairpin RNAs in Mammalian Cells, *Cell Biology*, 2002, pp. 6047-6052, vol. 99(9).
Zheng, L., et al., An Approach to Genomewide Screens of Expressed Small Interfering RNAs in Mammalian Cells, *Cell Biology*, 2004, pp. 135-140, vol. 101(1).

* cited by examiner

*Primary Examiner* — Li Zheng
(74) *Attorney, Agent, or Firm* — Pioneer Hi-Bred Int'l., Inc.

(57) ABSTRACT

Compositions and methods for modulating expression of gene products are provided. Compositions comprise suppression cassettes that comprise a convergent promoter pair operably linked to a silencing element that, upon expression, is capable of decreasing the expression of one or more target polynucleotides of interest. Compositions of the invention also include transformed plants, plant cells, plant tissues, and plant seeds. Methods of transformation and regeneration of plants comprising the novel constructs are provided. The methods find use in regulating gene expression, particularly genes associated with agronomic traits of interest. Further provided are promoter sequences, cells, plants, and vectors comprising these promoter sequences and methods of their use.

6 Claims, 14 Drawing Sheets

Ratio of Ara/Xyl

- The arabinose to xylose ratio decreases in all transgenic kernels relative to WT kernels.

Fig. 9 Total hemicellulose decreases in all transgenic relative to WT kernels.

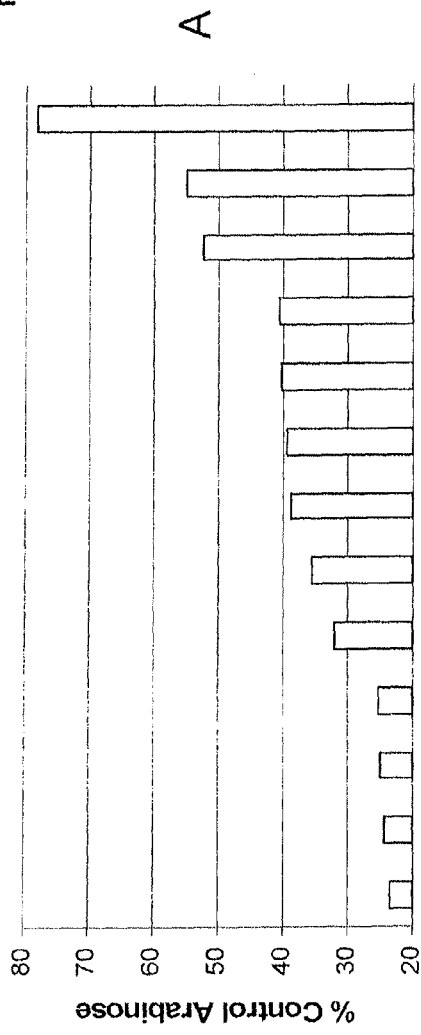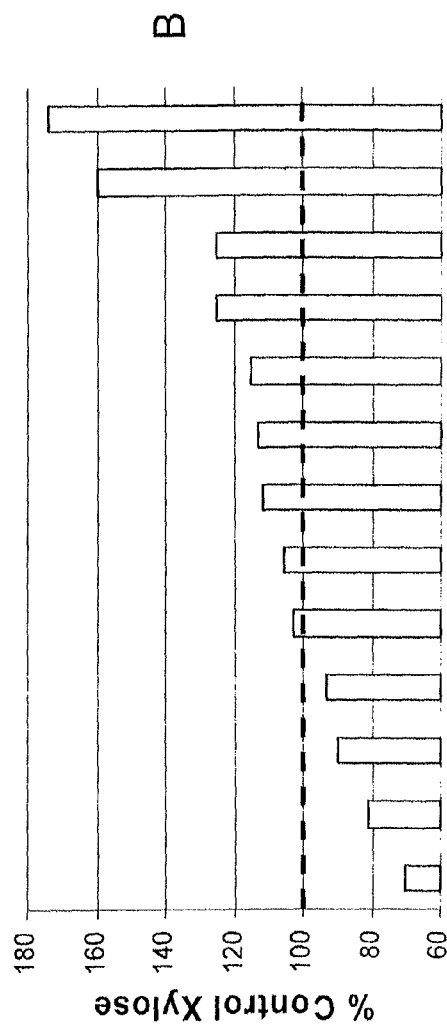
Fig. 10

Arabinose + Xylose

- Arabinose+xylose decreases in 12 transgenic events relative to wild type events.

```
                          SEQUENCE LISTING

<160> NUMBER OF SEQ ID NOS: 3

<210> SEQ ID NO 1
<211> LENGTH: 3590
<212> TYPE: DNA
<213> ORGANISM: Artificial Sequence
<220> FEATURE:
<223> OTHER INFORMATION: Suppression cassette comprising the GZ-W64A
      promoter linked to the RGP silencing element,
      linked to the OLE promoter.
<220> FEATURE:
<221> NAME/KEY: promoter
<222> LOCATION: (1)...(1483)
<223> OTHER INFORMATION: GZ-W64a promoter
<220> FEATURE:
<221> NAME/KEY: promoter
<222> LOCATION: (2635)...(3590)
<223> OTHER INFORMATION: Oleosin promoter
<220> FEATURE:
<221> NAME/KEY: misc_feature
<222> LOCATION: (1491)...(2634)
<223> OTHER INFORMATION: RGP1 silencing element

<400> SEQUENCE: 1
cgtatcacct atctaaataa gtcacgggag tttcgaacgt ccacttcgtc gcacggaatt     60
gcatgtttct tgttggaagc atattcacgc aatctccaca cataaaggtt tatgtataaa    120
cttacattta gctcagttta attacagtct tatttggatg catatgtatg gttctcaatc    180
catataagtt agagtaaaaa ataagtttaa attttatctt aattcactcc aacatatatg    240
gatctacaat actcatgtgc atccaaacaa actacttata ttgaggtgaa tttggtagaa    300
attaaactaa cttacacact aagccaatct ttactatatt aaagcaccag tttcaacgat    360
cgtcccgcgt caatattatt aaaaaactcc tacatttctt tataatcaac ccgcactctt    420
ataatctctt ctctactact ataataagag agtttatgta caaaataagg tgaaattatc    480
tataagtgtt ctggatattg gttgttggct cccatattca cacaacctaa tcaatagaaa    540
acatatgttt tattaaaaca aaatttatca tatatcatat atatatatat atcatatata    600
tatataaacc gtagcaatgc acgggcatat aactagtgca acttaataca tgtgtgtatt    660
aagatgaata agagggtatc caaataaaaa acttgttgct tacgtatgga tcgaaagggg    720
ttggaaacga ttaaacgatt aaatctcttc ctagtcaaaa ttgaatagaa ggagatttaa    780
tatatcccaa tccccttcga tcatccaggt gcaaccgtat aagtcctaaa gtggtgagga    840
acacgaaaga accatgcatt ggcatgtaaa gctccaagaa tttgttgtat ccttaacaac    900
tcacagaaca tcaaccaaaa ttgcacgtca agggtattgg gtaagaaaca atcaaacaaa    960
```

```
tcctctctgt gtgcaaagaa acacggtgag tcatgccgag atcatactca tctgatatac    1020
atgcttacag ctcacaagac attacaaaca actcatattg cattacaaag atcgtttcat    1080
gaaaaataaa ataggccgga caggacaaaa atccttgacg tgtaaagtaa atttacaaca    1140
aaaaaaaagc catatgtcaa gctaaatcta attcgtttta cgtagatcaa caacctgtag    1200
aaggcaacaa aactgagcca cgcagaagta cagaatgatt ccagatgaac catcgacgtg    1260
ctacgtaaag agagtgacga gtcatataca tttggcaaga aaccatgaag ctgcctacag    1320
ccgtatcggt ggcataagaa cacaagaaat tgtgttaatt aatcaaagct ataaataacg    1380
ctcgcatgcc tgtgcacttc tccatcacca ccactgggtc ttcagaccat tagctttatc    1440
tactccagag cgcagaagaa cccgatcgac agatatcgga tccatggaga tccatggcgg    1500
gcacggtgac ggtcccgggg tcgtcgaccc cctccacgcc gctgctcaag gacgagctcg    1560
acatcgtgat cccgacgatc cgcaacctcg acttcctgga gatgtggcgg cccttcttcc    1620
agccctacca cctcatcatc gtgcaggacg gcgacccgac caagaccatc aaggtgcccg    1680
agggcttcga ctacgaactc tacaaccgca acgacatcaa ccgcatcctc gggcccatcg    1740
atatccgcgg gcatgcctgc aggtcgactc tagaacgaag gggttgctag ccttgctgtg    1800
ccagatgtat ggcaggccag tcttgactcc caggctcagg tggtcgcaga tgaccttcac    1860
acaccatcct gcccacatgt cgtcgtagcg accgatgggc tggccatcac ccatgagacc    1920
aaagtacata gcagggccaa tgagatccct gtcgaaggca aggttcatgc cacacatggg    1980
gaacaaggtt cccttgggga ttgtcatgac agcatcaaca tacctctcat tcctctcctt    2040
gggcttgacc agctgtgtgg gagcatcata gtcaggdatg ttcagccaca ggccgtggga    2100
gacggcggtg tgagcaccct ccctgaggct gaagggdtat ccacgcacaa agtcagcacc    2160
ctcacggtag gggtcgtaca gggtgttgaa gaagaacggg gtggatgggc tgaggaggtt    2220
cttgatgtgc tgctcaagag cattgatatc cttgccagat gggtccttgg caacgaagca    2280
gtcgtcgtcg atggtgtaga tgtacttctt cttggagacc atgtagccga agcagcggca    2340
ggcggagtcc ttgaaggaga tgcaggaggc cttgggcccg aggatgcggt tgatgtcgtt    2400
gcggttgtag agttcgtagt cgaagccctc gggcaccttg atggtcttgg tcgggtcgcc    2460
gtcctgcacg atgatgaggt ggtagggctg gaagaagggc cgccacatct ccaggaagtc    2520
gaggttgcgg atcgtcggga tcacgatgtc gagctcgtcc ttgagcagcg cgtggaggg    2580 ggtcgacgac cccgggaccg tcaccgtgcc cgccatggat ctgttaaccc atggtagcgc    2640
tagcagagcg agctaggtac cccacgtgcg cacgctgccc agagctcctg ccgctgccgc    2700
tgccgctgat gcttgagcta cgactacgag tgaggtagat gagggcgagg gagagctggg    2760
tgtttataga gggcgtggca acgcgcggag gcgggatctg gcgcggccgc gtgggacgca    2820
tgcgggactc gtgtcggggg cagcgcgaca cctgtgtagg gggtgtcgag gacaaggctt    2880
cctcggtcgc gccgcttccg cgcggcgata tatacgaggt tgtgtgtgtg cgcgcacttc    2940
cgttggatcg gccgctggtt gccggaggtg gcggggccga atctcatgtg ggccgtagtc    3000
cgggcctctt ttacttcttt tgtcttccgt gtctcactat tttctggtcc acgtagacct    3060
acatcacata ctagcaagaa ctagtaaaag catctgagcg tcagtatagt tttagtatat    3120
taataataat atagatttat tgtgactaaa atataaatttg tggaaacaat gtgcttggta    3180
cctgttgaga ttgggtgaag aactacagca tgacaacata tttaaattga ggacacttcc    3240
tctcttctcc gaagaggatg aatggtaggg tgtccagaaa acaaatttgt atatcgaaac    3300
tcatgagaag ttacgaagcg taaaatatgg attatcgtaa ttatttgctg aaggtgagat    3360
```

```
gcatgttctc tcaatcgatt aaccgtgtaa tgctcattgc caataataat atcctaggga    3420
aagactcgat atatgatgaa agacaagaca acaataatct tcgccatctt ataccttggg    3480
aggttctcta aacaggggt acacgggcgt agggatacag gaatgccaat cccgatagca    3540
gatatatttg aggtgtttgg gtttggagga atgagatagt caatcggatc              3590

<210> SEQ ID NO 2
<211> LENGTH: 1143
<212> TYPE: DNA
<213> ORGANISM: Artificial Sequence
<220> FEATURE:
<223> OTHER INFORMATION: RGP1 silencing element

<400> SEQUENCE: 2
ccatggcggg cacggtgacg gtcccgggt cgtcgacccc ctccacgccg ctgctcaagg      60
acgagctcga catcgtgatc ccgacgatcc gcaacctcga cttcctggag atgtggcggc    120
ccttcttcca gccctaccac ctcatcatcg tgcaggacgg cgaccccgacc aagaccatca  180 aggtgcccga gggcttcgac tacgaactct acaaccgcaa cgacatcaac cgcatcctcg   240
ggcccatcga tatccgcggg catgcctgca ggtcgactct agaacgaagg ggttgctagc   300
cttgctgtgc cagatgtatg gcaggccagt cttgactccc aggctcaggt ggtcgcagat   360
gaccttcaca caccatcctg cccacatgtc gtcgtagcga ccgatgggct ggccatcacc   420
catgagacca aagtacatag cagggccaat gagatccctg tcgaaggcaa ggttcatgcc   480
acacatgggg aacaaggttc ccttgggat tgtcatgaca gcatcaacat acctctcatt    540
cctctccttg ggcttgacca gctgtgtggg agcatcatag tcagggatgt tcagccacag   600
gccgtgggag acggcggtgt gagcacctc cctgaggctg aaggggtatc cacgcacaaa    660
gtcagcaccc tcacggtagg ggtcgtacag ggtgttgaag aagaacgggg tggatgggct   720
gaggaggttc ttgatgtgct gctcaagagc attgatatcc ttgccagatg ggtccttggc   780
aacgaagcag tcgtcgtcga tggtgtagat gtacttcttc ttggagacca tgtagccgaa   840
gcagcggcag gcggagtcct tgaaggagat gcaggaggcc ttgggcccga ggatgcggtt   900
gatgtcgttg cggttgtaga gttcgtagtc gaagccctcg ggcaccttga tggtcttggt   960
cgggtcgccg tcctgcacga tgatgaggtg gtagggctgg aagaagggcc gccacatctc  1020
caggaagtcg aggttgcgga tcgtcgggat cacgatgtcg agctcgtcct tgagcagcgg  1080
cgtggagggg gtcgacgacc ccgggaccgt caccgtgccc gccatggatc tgttaaccca  1140
tgg                                                                 1143

<210> SEQ ID NO 3
<211> LENGTH: 559
<212> TYPE: DNA
<213> ORGANISM: Zea mays
<220> FEATURE:
<221> NAME/KEY: promoter
<222> LOCATION: (0)...(0)
<223> OTHER INFORMATION: Glb2 promoter

<400> SEQUENCE: 3
cgaattttat agaaactggc tgaaaagctg rgtgtttcgt agtctgcaac agcttttggt     60
agcaagaagc tgcgaaaagc cgaaacaaac aacgacttta tcttctttag cacataaatg   120
gtataaaaaa atgtcgtaac agctatttt ttaagaatcc agtttctcgg agatctttgg    180
aaaaaagttc tctgaaacag ccccgcgycg ctacgtgcag ctccatctgc tccgtgttgt   240
ccccacccca atcaccgctg tcgcttcgcc gcaggcatcc cagcagcgag ctagcatgca   300
```

```
cgcacgcacg caagcacacg gcggcagctg cacggatgcg gccgagtgcg gcagcacagc    360
agcgcgcgcg cgctccacat cgccttcgct agttcgctcc gccacgtacg cggcccggcc    420
tccacctggc ggcgcgcatg gctgcgaccc tcgccgcgcc acctcttcat atacgctgca    480
gctcgcctcg aaccytcgca tcgaacgcac actcgcactc gcacgtacac cacactagtt    540
accacagtcg acgggcgcc                                                 559
```

COMPOSITIONS AND METHODS FOR MODULATING EXPRESSION OF GENE PRODUCTS

CROSS-REFERENCE TO RELATED APPLICATIONS

This application is a continuation of U.S. application Ser. No. 12/569,213, filed Sep. 29, 2009, now U.S. Pat. No. 8,404,929, which is a continuation of U.S. application Ser. No. 11/513,330, filed on Aug. 29, 2006, which claims the benefit of U.S. Provisional Application No. 60/712,354, filed on Aug. 30, 2005, both of which are herein incorporated by reference in their entirety.

FIELD OF THE INVENTION

The present invention is drawn to the field of genetics and molecular biology. More particularly, the compositions and methods are directed to modulation of gene function.

REFERENCE TO A SEQUENCE LISTING SUBMITTED AS A TEXT FILE VIA EFS-WEB

The official copy of the sequence listing is submitted electronically via EFS-Web as an ASCII formatted sequence listing with a file named 429313SEQLIST.txt, created on Feb. 20, 2013, and having a size of 7.2 KB and is filed concurrently with the specification. The sequence listing contained in this ASCII formatted document is part of the specification and is herein incorporated by reference in its entirety.

BACKGROUND OF THE INVENTION

RNA interference (RNAi) is a phenomenon in which small double-stranded RNA molecules induce sequence-specific degradation of homologous single-stranded RNA. RNAi has been used as a tool to degrade mRNA in cells to shut down the effect of specific genes in many cell-types. In this approach to control gene expression, double-stranded RNAs that are complimentary to known mRNA's are introduced into a cell to specifically target and destroy that particular mRNA. Once double stranded RNA (dsRNA) enters the cell, it is cleaved by a ribonuclease enzyme, dicer, into double stranded small interfering RNAs (siRNAs). The siRNAs become integrated into a multi-subunit protein complex which guides the siRNAs to the target RNA sequence.

In plants, RNAi can be induced through microinjection of long double-stranded RNA or by introduction of DNA constructs that may be transcribed into such double-stranded RNA molecules. The double-stranded RNA is cleaved into RNA fragments of about 19 to 23 nucleotides called interfering RNAs (siRNAs). siRNAs are incorporated into a ribonuclease enzyme complex known as the RNA-induced silencing complex (RISC). The antisense strand of siRNA within the RISC pathway serves as a guide for sequence-specific degradation of homologous messenger RNAs.

The ability of transfected synthetic small interfering RNAs to suppress the expression of specific transcripts has proven to be a useful tool to study gene function. Recently short hairpin RNAs (shRNAs) have been shown to result in gene silencing as effectively as short dsRNAs. Several DNA-based vectors have been developed that direct transcription of small hairpin RNAs (shRNAs). These RNAs are processed into functional siRNAs by cellular enzymes. RNAi vectors for the expression of shRNAs are available. These vectors typically use RNA polymerase III (Pol III) to express short hairpin RNAs. These transcripts adopt stem-loop structures that are processed into siRNAs by the RNAi machinery.

Other vectors have been developed that drive expression of both the sense and antisense strands of a DNA construct separately. The transcripts hybridize in vivo to make the siRNA. In efforts to induce long-term gene silencing, expression vectors that continually express siRNAs in stably transfected cells have been used.

Presently, silencing genes in more than one tissue requires the use of two separate expression cassettes. This approach takes up valuable space in a molecular stack, increasing the regulatory burden for sequence and expression confirmation, as well as, the potential for undesirable rearrangements and deletions. Currently available promoters, particularly tissue-preferred promoters, may not cover the entire temporal range of expression need to achieve the trait goals. Methods and compositions are needed that avoid these complications and allow for differential expression or the increased time-frame of expression of a silencing element without an increase in the size of the expression cassette.

BRIEF SUMMARY OF THE INVENTION

Compositions and methods are provided for modulating the expression and function of target polynucleotides of interest and the polypeptides they encode in an organism. Compositions of the invention include suppression cassettes comprising a silencing element, having homology to at least one target polynucleotide of interest. The silencing element is transcribed as a hairpin RNA and is flanked and operably linked to convergent promoters such that each promoter is capable of driving expression of the silencing element in opposite directions.

A variety of promoters may be used in the suppression cassettes. While any promoter may be used in the suppression cassette, generally the cassette is designed such that the promoters have a different expression profile. That is, the promoters drive expression in different tissues or at different developmental stages of an organism. Thus, by the choice of promoters, temporal and tissue expression of the transcripts can be controlled. In the same manner, to more effectively control a disease, the promoters may be chosen to be expressed at different stages of a disease or pathogen infection.

Compositions of the invention also include transformed organisms such as plants, animals (mammals, humans, etc), bacteria, and fungi comprising the suppression cassettes of the invention as well as transformed cells of such organisms. Compositions of the invention also include plant cells, plant tissues, plants, and plant seeds comprising the suppression cassettes of the invention stably incorporated in their genome.

Methods of the invention comprise the use of these suppression cassettes to provide for expression of inhibitory RNA molecules, including double-stranded RNA, hairpin RNA, intron-containing hairpin RNA, stem-loop RNA, and the like, that have been designed to inhibit expression of at least one polynucleotide of interest at different times or in different tissues. Also included are methods of transformation and regeneration of plants comprising the recombinant constructs of the invention.

The compositions and methods of the invention are useful for decreasing expression and function of gene products of interest, thereby altering the phenotype of an organism or cell of interest. In some embodiments, the construct can be used to improve characteristics of commercially important plants and plant parts. Thus, the compositions and methods can be used to improve the yield and quality of desirable plant products thereby improving agronomic efficiency. In other embodiments, genes that are indicative of disease states in a mammal, such as cancer genes, may be targeted.

Further provided are compositions and methods for regulating expression of a heterologous nucleotide sequence of interest in a plant or plant cell. Compositions comprise novel polynucleotides for promoters that initiate transcription. Embodiments of the invention comprise the polynucleotide set forth in SEQ ID NO:3 or a complement thereof; a nucleotide sequence comprising at least 20 contiguous nucleotides of SEQ ID NO:3, wherein said sequence initiates transcription in a plant cell; and, a nucleotide sequence comprising a sequence having at least 85% sequence identity to the sequence set forth in SEQ ID NO:3, wherein said sequence initiates transcription in the plant cell.

A method for expressing a heterologous nucleotide sequence in a plant or plant cell is provided. The method comprises introducing into a plant or a plant cell an expression cassette comprising a heterologous nucleotide sequence interest operably linked to one of the promoters of the present invention. In this manner, the promoter sequences are useful for controlling the expression of the operably linked heterologous nucleotide sequence. In specific methods, the heterologous nucleotide sequence of interest is expressed in an embryo-preferred manner.

Further provided is a method for expressing a nucleotide sequence of interest in an embryo-preferred manner in a plant. The method comprises introducing into a plant cell an expression cassette comprising a promoter of the invention operably linked to a heterologous nucleotide sequence of interest.

Expression of the nucleotide sequence of interest can provide for modification of the phenotype of the plant. Such modification includes modulating the production of an endogenous product, as to amount, relative distribution, or the like, or production of an exogenous expression product to provide for a novel function or product in the plant. In specific methods and compositions, the heterologous nucleotide sequence of interest comprises a gene product that confers herbicide resistance, pathogen resistance, insect resistance, and/or altered tolerance to salt, cold, or drought.

Expression cassettes comprising the promoter sequences of the invention operably linked to a heterologous nucleotide sequence of interest are provided. Additionally provided are transformed plant cells, plant tissues, seeds, and plants.

BRIEF DESCRIPTION OF THE DRAWINGS

FIG. 10 depicts the arabinose (A) and xylose (B) concentrations (as a percent of control) for transgenic kernels comprising the RGP-1 suppression construct. Analyses were as described for FIG. 9.

DETAILED DESCRIPTION OF THE INVENTION

Figure 1:
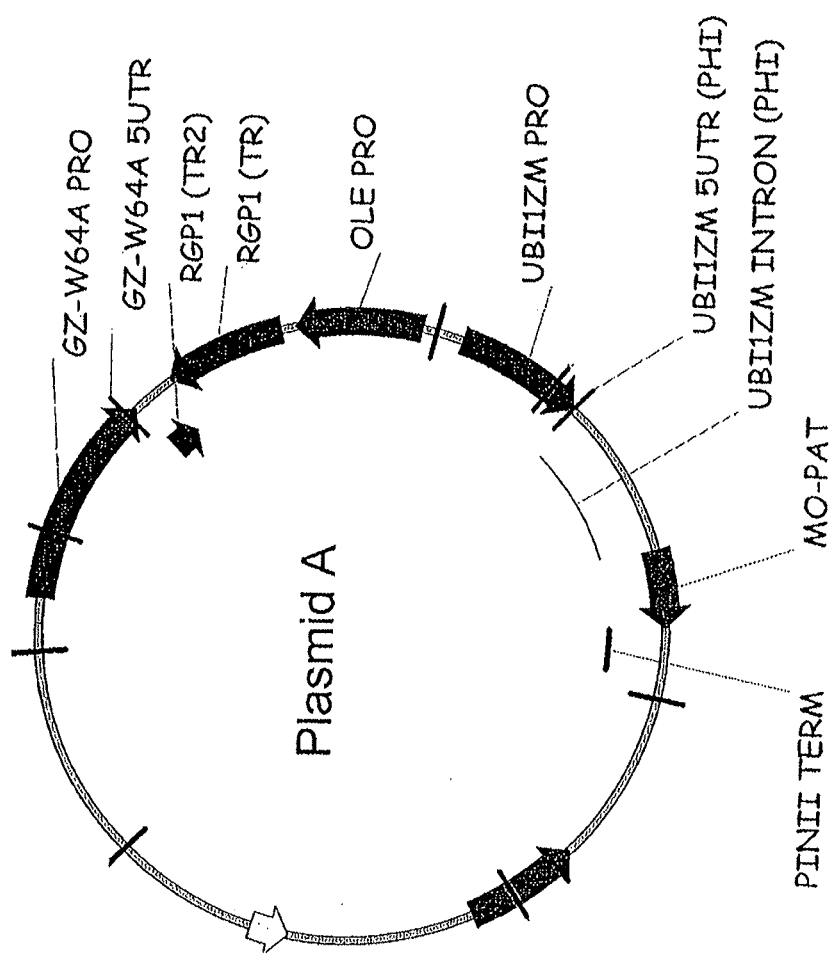
FIG. 1 depicts a plasmid (Plasmid A) comprising a suppression cassette having a silencing element comprising an RGP1 inhibitory sequence (SEQ ID NO:2) under dual control by a gamma-zein promoter and an oleosin promoter. The RGP1 inhibitory sequence comprises a truncated RGP1 region (TR1) from the 5' end of the RGP1 coding sequence (U.S. Pat. No. 6,194,638) and a second truncated RGP1 region (TR2) also from the 5' end of the RGP1 coding sequence but which is ligated into the silencing element of the suppression cassette such that the second fragment is in reverse orientation relative to the first RGP1 fragment.

I. Suppression Cassettes and Methods of Use

The present invention is drawn to compositions and methods for modulating expression of gene products in organisms such as plants, animals, fungi, and bacteria. Compositions of the invention comprise a recombinant construct referred to herein as a suppression cassette. The suppression cassette comprises a silencing element flanked at both ends by promoters capable of driving expression of the silencing element. That is, each promoter is "operably linked" to the silencing element. The two promoters flanking the silencing element are capable of controlling gene expression in different tissues or types of cells as well as in different stages of development depending on the choice of promoters.

By "silencing element" is intended a polynucleotide which when expressed in a host cell, is capable of reducing or eliminating the level of a target polynucleotide or the polypeptide encoded thereby. The silencing element employed can reduce or eliminate the level of the target sequence by influencing the level of the target RNA transcript or, alternatively, by influencing translation and thereby affecting the level of the encoded polypeptide. Methods to assay for functional silencing elements that are capable of reducing or eliminating the level of a sequence of interest are disclosed elsewhere herein. A single suppression cassette employed in the invention can harbor one or more silencing elements which, as discussed in further detail below, are designed to decrease the level of expression of the same or different target polynucleotides. The RNA transcripts of the silencing element, after self-pairing, comprise regions of double-stranded RNA and are referred to herein interchangeably as "inhibitory RNA transcripts" or "inhibitory RNA molecules." These inhibitory RNA transcripts can decrease the level of one or more target polynucleotide of interest.

Methods for designing silencing elements that express a hairpin structure and its use in RNA interference to decrease or silence the expression of genes are described, for example, in Chuang and Meyerowitz (2000) *Proc. Natl. Acad. Sci. USA* 97:4985-90; Stoutjesdijk et al. (2002) *Plant Physiology* 129: 1723-31; Waterhouse and Helliwell (2003) *Nat. Rev. Gen.* 4:29-38; Pandolfini et al. *BMC Biotechnology* 3:7, and U.S. Patent Application Publication No. 20030175965, each of which is herein incorporated by reference. For hairpin RNA (hpRNA) interference, the silencing element traditionally is designed to express an RNA transcript that pairs with itself to form a hairpin structure that comprises a single-stranded loop region and a base-paired stem. hpRNA molecules are highly efficient at inhibiting the expression of endogenous genes, and the RNA interference they induce is inherited by subsequent generations of plants. A transient assay for the efficiency of hpRNA constructs to silence gene expression in vivo has been described by Panstruga et al. (2003) *Mol. Biol. Rep.* 30:135-40, herein incorporated by reference.

In specific embodiments, the silencing element employed in the methods and compositions of the invention comprises in the following order, a first segment, a second segment, and a third segment, where the first and the third segment share sufficient complementarity to allow the transcribed RNA to form a double-stranded stem-loop structure. "Stem and loop structure" and "stem-loop structure" are used synonymously herein and are intended to mean a single RNA polynucleotide molecule wherein a region closer to the 5' end of the molecule pairs with a self-complementary region closer to the 3' end of the molecule to form a double-stranded RNA region (known as the stem or "arms" of the structure) while an intervening region between the 5' and 3' self-complementary regions remains unpaired (known as the "loop"). An RNA hairpin structure is an example of a stem-loop structure capable of causing RNA interference.

The "second segment" of the hairpin comprises a "loop" or a "loop region." These terms are used synonymously herein and are to be construed broadly to comprise any nucleotide sequence that confers enough flexibility to allow self-pairing to occur between complementary regions of a polynucleotide (i.e., segments 1 and 2 which form the stem of the hairpin). For example, in some embodiments, the loop region may be substantially single stranded and act as a spacer between the self-complementary regions of the hairpin stem-loop. In some embodiments, the loop region can comprise a random or nonsense nucleotide sequence and thus not share sequence identity to a target polynucleotide. In other embodiments, the loop region comprises a sense or an antisense RNA sequence or fragment thereof that shares identity to a target polynucleotide. See, for example, International Patent Publication No. WO 02/00904, herein incorporated by reference.

In some embodiments, the loop region can comprise one or more spliceable introns. In such constructs (referred to as ihpRNA), the inhibitory RNA transcripts have the same general structure as the hpRNA, but the RNA molecule additionally comprises an intron that is capable of being spliced in the cell in which the ihpRNA is expressed. For intron-containing hairpin RNA (ihpRNA), the inhibitory polynucleotides have the same general structure as for hpRNA, but the RNA molecule additionally comprises an intron that is capable of being spliced in the cell in which the ihpRNA is expressed. See, for example, Smith et al. (2000) *Nature* 407:319-320; Wesley et al. (2001) *The Plant Journal* 27:581-590; Wang and Waterhouse (2001) *Current Opinion in Plant Biology* 5:146-150; Waterhouse and Helliwell (2003) *Nat. Rev. Gen.* 4:29-38; Helliwell and Waterhouse (2003) *Methods* 30:289-95, and U.S. Patent Publication No. 20030180945, each of which is herein incorporated by reference. Any intron that is spliced may be used according to the invention. Non-limiting examples of introns that may be used include the orthophosphate dikinase 2 intron 2 (pdk2 intron) described in U.S. Patent Application Publication No. 20030180945, the catalase intron from castor bean (GenBank Accession No. AF274974), the delta-12 desaturase (FAD2) intron from cotton (GenBank Accession No. AF331163), the delta-12 desaturase (FAD2) intron from *Arabidopsis* (GenBank Accession No. AC069473), the ubiquitin intron from maize (GenBank Accession No. S94464), an actin intron from rice, the maize ADHI intron1, the potato ST-LS1 intron2.

When the loop region (i.e., the second segment) does not contain an intron, it can be optimized to be as short as possible while still providing enough intramolecular flexibility to allow the formation of the base-paired stem region. Accordingly, the loop sequence is generally less than 1000 nucleotides, less than 900 nucleotides, less than 800 nucleotides, less than 700 nucleotides, less than 600 nucleotides, less than 500 nucleotides, less than 400 nucleotides, less than 300 nucleotides, less than 200 nucleotides, less than 100 nucleotides, less than 50 nucleotides, less than 25 nucleotides, less than 20 nucleotides, less than 15 nucleotides or about 10 nucleotides or less.

The "first" and the "third" segment of the hairpin RNA molecule comprise the base-paired stem of the hairpin structure. The first and the third segments are inverted repeats of one another and share sufficient complementarity to allow the formation of the base-paired stem region. In specific embodiments, the first and the third segments are fully complementary to the one another. Alternatively, the first and the third segment may be partially complementary to each other so long as they are capable of hybridizing to one another to form a base-paired stem region. The amount of complementarity between the first and the third segment can be calculated as a percentage of the entire segment. Thus, the first and the third segment of the hairpin RNA generally share at least 50%, 60%, 70%, 80%, 85%, 90%, 91%, 92%, 93%, 94%, 95%, 96%, 97%, 98%, 99%, up to and including 100% complementarity.

The first and the third segment are at least about 1000, 500, 400, 300, 200, 100, 50, 40, 30, 25, 20, 15 or 10 nucleotides in length. In specific embodiments, the length of the first and/or the third segment is about 10-100 nucleotides, about 10 to about 75 nucleotides, about 10 to about 50 nucleotides, about 10 to about 40 nucleotides, about 10 to about 35 nucleotides, about 10 to about 30 nucleotides, about 10 to about 25 nucleotides, about 10 to about 20 nucleotides. In other embodiments, the length of the first and/or the third segment comprises at least 10-20 nucleotides, 20-35 nucleotides, 30-45 nucleotides, 40-50 nucleotides, 50-100 nucleotides, or 100-300 nucleotides. See, for example, International Publication No. WO 0200904. In specific embodiments, the first and the third segment comprises at least 20 nucleotides having at least 85% complementary to the first segment. In still other embodiments, the first and the third segments which form the stem-loop structure of the hairpin comprises 3' or 5' overhang regions having unpaired nucleotide residues.

In specific embodiments, the sequences used in the first, the second, and/or the third segments comprise domains that are designed to have sufficient sequence identity to a target polynucleotide of interest and thereby have the ability to decrease the level of expression of the target polynucleotide. The specificity of the inhibitory RNA transcripts is therefore generally conferred by these domains of the silencing element. Thus, in some embodiments of the invention, the first, second and/or third segment of the silencing element comprise a domain having at least 10, at least 15, at least 19, at least 20, at least 21, at least 22, at least 23, at least 24, at least 25, at least 30, at least 40, at least 50, at least 100, at least 200, at least 300, at least 500, at least 1000, or more than 1000 nucleotides that share sufficient sequence identity to the target polynucleotide to allow for a decrease in expression levels of the target polynucleotide when expressed in an appropriate cell. In other embodiments, the domain is between about 15 to 50 nucleotides, about 20-35 nucleotides, about 25-50 nucleotides, about 20 to 75 nucleotides, about 40-90 nucleotides about 15-100 nucleotides. In specific embodiments, the domain of the first, the second, and/or the third segment has 100% sequence identity to the target polynucleotide. In other embodiments, the domain of the first, the second and/or the third segment having homology to the target polypeptide have at least 50%, 60%, 70%, 80%, 85%, 90%, 91%, 92%, 93%, 94%, 95%, 96%, 97%, 98%, 99%, or greater sequence identity to a region of the target polynucleotide. The sequence identity of the domains of the first, the second and/or the third segments to the target polynucleotide need only be sufficient to decrease expression of the target polynucleotide of interest.

The amount of complementarity shared between the first, second, and/or third segment and the target polynucleotide or the amount of complementarity shared between the first segment and the third segment (i.e., the stem of the hairpin structure) may vary depending on the organism in which gene expression is to be controlled. Some organisms or cell types may require exact pairing or 100% identity, while other organisms or cell types may tolerate some mismatching. In some cells, for example, a single nucleotide mismatch in the targeting sequence abrogates the ability to suppress gene expression. In these cells, the suppression cassettes of the invention can be used to target the suppression of mutant genes, for example, oncogenes whose transcripts comprise point mutations and therefore they can be specifically targeted using the methods and compositions of the invention without altering the expression of the remaining wild-type allele.

Any region of the target polynucleotide can be used to design the domain of the silencing element that shares sufficient sequence identity to allow expression of the hairpin transcript to decrease the level of the target polynucleotide. For instance, the domain can be designed to share sequence identity to the 5' untranslated region of the target polynucleotide(s), the 3' untranslated region of the target polynucleotide(s), exonic regions of the target polynucleotide(s), intronic regions of the target polynucleotide(s), and any combination thereof. In some instances to optimize the siRNA sequences employed in the hairpin, the synthetic oligodeoxyribonucleotide/RNAse H method can be used to determine sites on the target mRNA that are in a conformation that is susceptible to RNA silencing. See, for example, Vickers et al. (2003) *J. Biol. Chem.* 278:7108-7118 and Yang et al. (2002) *Proc. Natl. Acad. Sci. USA* 99:9442-9447, herein incorporated by reference. These studies indicate that there is a significant correlation between the RNase-H-sensitive sites and sites that promote efficient siRNA-directed mRNA degradation.

It is recognized that multiple members of a gene family can be targeted using this method. For example, a silencing element can be designed, based on sequence identity shared among various members of a gene family, and thereby decrease the expression of multiple related polynucleotides. Alignment of the family members can be used to design such a silencing element.

It is further recognized that multiple unrelated target polynucleotides can also be targeted. For example, where the purpose is to decrease the level of expression of more than one target polynucleotide, regions of DNA whose sequence corresponds to that present in the different target polynucleotides can be combined into the first, second, and/or third segment of the silencing element. In this manner, the suppression cassette is designed to express a single fusion RNA transcript having specificity for multiple target polynucleotides.

In some embodiments, the second segment (i.e., the loop region) may comprise all or part of a sequence corresponding to a target polynucleotide of interest. While the stem structure (i.e., the first and third segment) of the hairpin transcript will, in most instances, be designed to target a gene product, it is contemplated that the base-paired stem structure of the inhibitory RNA transcript may be formed by the hybridization of a first segment and a second segment, neither of which correspond to an endogenous sequence found in the organism of interest.

The following terms are used to describe the sequence relationships between two or more polynucleotides: (a) "reference sequence", (b) "comparison window", (c) "sequence identity", and, (d) "percentage of sequence identity".

(a) As used herein, "reference sequence" is a defined sequence used as a basis for sequence comparison. A reference sequence may be a subset or the entirety of a specified sequence; for example, as a segment of a full-length cDNA or gene sequence, or the complete cDNA or gene sequence.

(b) As used herein, "comparison window" makes reference to a contiguous and specified segment of a polynucleotide sequence, wherein the polynucleotide sequence in the comparison window may comprise additions or deletions (i.e., gaps) compared to the reference sequence (which does not comprise additions or deletions) for optimal alignment of the two polynucleotides. Generally, the comparison window is at least 20 contiguous nucleotides in length, and optionally can be 30, 40, 50, 100, or longer. Those of skill in the art understand that to avoid a high similarity to a reference sequence due to inclusion of gaps in the polynucleotide sequence a gap penalty is typically introduced and is subtracted from the number of matches.

Methods of alignment of sequences for comparison are well known in the art. Thus, the determination of percent sequence identity between any two sequences can be accomplished using a mathematical algorithm. Non-limiting examples of such mathematical algorithms are the algorithm of Myers and Miller (1988) *Comput. Appl. Biosci.* 4:11-17; the local alignment algorithm of Smith et al. (1981) *Adv. Appl. Math.* 2:482; the global alignment algorithm of Needleman and Wunsch (1970) *J. Mol. Biol.* 48:443-453; the search-for-local alignment method of Pearson and Lipman (1988) *Proc. Natl. Acad. Sci. USA* 85:2444-2448; the algorithm of Karlin and Altschul (1990) *Proc. Natl. Acad. Sci. USA* 872264, modified as in Karlin and Altschul (1993) *Proc. Natl. Acad. Sci. USA* 90:5873-5877.

Computer implementations of these mathematical algorithms can be utilized for comparison of sequences to determine sequence identity. Such implementations include, but are not limited to: CLUSTAL in the PC/Gene program (available from Intelligenetics, Mountain View, Calif.); the ALIGN program (Version 2.0) and GAP, BESTFIT, BLAST, FASTA, and TFASTA in the GCG Wisconsin Genetics Software Package, Version 10 (available from Accelrys Inc., 9685 Scranton Road, San Diego, Calif., USA). Alignments using these programs can be performed using the default parameters. The CLUSTAL program is well described by Higgins et al (1988) *Gene* 73:237-244 (1988); Higgins et al. (1989) *Comput. Appl Biosci.* 5:151-153; Corpet et al, (1988) *Nucleic Acids Res.* 16:10881-90; Huang et al. (1992) *CABIOS* 8:155-65; and Pearson et al. (1994) *Methods Mol. Biol.* 24:307-331. The ALIGN program is based on the algorithm of Myers and Miller (1988) supra. A PAM120 weight residue table, a gap length penalty of 12, and a gap penalty of 4 can be used with the ALIGN program when comparing amino acid sequences. The BLAST programs of Altschul et al. (1990) *J. Mol. Biol.* 215:403 are based on the algorithm of Karlin and Altschul (1990) supra. BLAST nucleotide searches can be performed with the BLASTN program, score=100, wordlength=12, to obtain nucleotide sequences homologous to a nucleotide sequence encoding a protein of the invention. To obtain gapped alignments for comparison purposes. Gapped BLAST (in BLAST 2.0) can be utilized as described in Altschul et al. (1997) *Nucleic Acids Res.* 25:3389. Alternatively, PSI-BLAST (in BLAST 2.0) can be used to perform an iterated search that detects distant relationships between molecules. See Altschul et al. (1997) supra. When utilizing BLAST, Gapped BLAST, PSI-BLAST, the default parameters of the respective programs (e.g., BLASTN for nucleotide sequences, BLASTX for proteins) can be used. See ncbi.nlm.nih.qov which can be accessed using the prefix www.; Alignment may also be performed manually by inspection.

Unless otherwise stated, sequence identity/similarity values provided herein refer to the value obtained using GAP Version 10 using the following parameters: % identity and % similarity for a nucleotide sequence using GAP Weight of 50 and Length Weight of 3, and the nwsgapdna.cmp scoring matrix; % identity and % similarity for an amino acid sequence using GAP Weight of 8 and Length Weight of 2, and the BLOSUM62 scoring matrix; or any equivalent program thereof. "Equivalent program" is intended to mean any sequence comparison program that, for any two sequences in question, generates an alignment having identical nucleotide or amino acid residue matches and an identical percent sequence identity when compared to the corresponding alignment generated by GAP Version 10.

GAP uses the algorithm of Needleman and Wunsch (1970) *J. Mol. Biol.* 48:443-453, to find the alignment of two complete sequences that maximizes the number of matches and minimizes the number of gaps. GAP considers all possible alignments and gap positions and creates the alignment with the largest number of matched bases and the fewest gaps. It allows for the provision of a gap creation penalty and a gap extension penalty in units of matched bases. GAP must make a profit of gap creation penalty number of matches for each gap it inserts. If a gap extension penalty greater than zero is chosen, GAP must, in addition, make a profit for each gap inserted of the length of the gap times the gap extension penalty. Default gap creation penalty values and gap extension penalty values in Version 10 of the GCG Wisconsin Genetics Software Package for protein sequences are 8 and 2, respectively. For nucleotide sequences the default gap creation penalty is 50 while the default gap extension penalty is 3. The gap creation and gap extension penalties can be expressed as an integer selected from the group of integers consisting of from 0 to 200. Thus, for example, the gap creation and gap extension penalties can be 0, 1, 2, 3, 4, 5, 6, 7, 8, 9, 10, 15, 20, 25, 30, 35, 40, 45, 50, 55, 60, 65, or greater.

GAP presents one member of the family of best alignments. There may be many members of this family, but no other member has a better quality. GAP displays four figures of merit for alignments: Quality, Ratio, Identity, and Similarity. The Quality is the metric maximized in order to align the sequences. Ratio is the quality divided by the number of bases in the shorter segment. Percent Identity is the percent of the symbols that actually match. Percent Similarity is the percent of the symbols that are similar. Symbols that are across from gaps are ignored. A similarity is scored when the scoring matrix value for a pair of symbols is greater than or equal to 0.50, the similarity threshold. The scoring matrix used in Version 10 of the GCG Wisconsin Genetics Software Package is BLOSUM62 (see Henikoff and Henikoff (1989) *Proc. Natl. Acad. Sci. USA* 89:10915).

(c) As used herein, "sequence identity" or "identity" in the context of two polynucleotides makes reference to the residues in the two sequences that are the same when aligned for maximum correspondence over a specified comparison window. A "complement sequence" in the context of two oppositely orientated polynucleotides make reference to the nucleotide residues which when aligned interact to form a double-stranded structure (i.e., the complementary sequence to 5'-G-T-A-C-3' is 3'-C-A-T-G-5').

(d) As used herein, "percentage of sequence identity" means the value determined by comparing two optimally aligned sequences over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base occurs in both sequences to yield the number of matched positions, dividing the number of matched positions by the total number of positions in the window of comparison, and multiplying the result by 100 to yield the percentage of sequence identity. As used herein "percent complementarity" means the value determined by comparing the complementarity of two oppositely orientated polynucleotides. The percentage is calculated by determining the number of positions at which the complement nucleic acid base occurs in both sequences to yield the number of complement positions, dividing the number of complement positions by the total number of positions in the window of comparison, and multiplying the result by 100 to yield the percentage of sequence complementarity.

The suppression cassettes disclosed herein comprise two convergent promoters that drive transcription of an operably linked silencing element. "Convergent promoters" refers to promoters that are oriented on either terminus of the operably linked silencing element such that each promoter drives transcription of the silencing element in opposite directions, yielding two transcripts. In specific embodiments, the promoters are chosen to provide differential expression of the respective transcripts.

The two convergent promoters within the suppression cassette are chosen to provide for different temporal and/or spatial patterns (i.e., different cell types and/or tissues) of expression of the hairpin RNA transcripts encoded by the silencing element. Likewise they can be chosen to be expressed in different cell types or tissues of an organism. Any combination of promoters can be used to direct the temporal and/or spatial expression of the operably linked silencing element in a host organism of interest as long as the promoters are capable of initiating transcription in the host cell. "Differential expression profiles" refers to two promoters capable of driving transcription of the same operably linked silencing element but having different time frames during which they operate to drive expression, such as during different developmental stages, growth stages, environmental conditions, etc., and/or to two promoters capable of driving transcription of the same operably linked silencing element but which provide for different spatial expression patterns, such as expression in different tissues, organs, cells, etc., or combinations thereof. The term "differential expression profile" is to be construed broadly, and thus the difference in expression profiles can range from almost entirely overlapping expression to mutually exclusive expression, as long as some difference in the expression profiles exists.

Where the organism is a plant, a differential expression profile can be achieved by selecting promoters that are under developmental control, such as promoters that initiate transcription preferentially in certain tissues, such as leaves, roots, fruit, seeds, or flowers. Alternatively, one or both of the convergent promoters can be an inducible promoter, for example, a chemical-inducible promoter wherein expression within the plant or part thereof is induced in response to exposure of the plant or part thereof to the chemical. In other embodiments, one or both of the convergent promoters can be induced by an environmental stimuli such as, but not limited to, drought, temperature, salinity, light, or disease. Of particular interest are tissue-preferred promoters that provide for spatially different expression profiles and can further provide for temporally different expression profiles.

Inducible promoters are known in the art and include, but are not limited to, that from the ACEI system, which responds to copper (Mett et al. (1993) *Proc. Natl. Acad. Sci. USA* 90:4567-4571 (1993)); the maize In2-2 promoter, which is activated by benzenesulfonamide herbicide safeners (Hershey et al. (1991) *Mol. Gen. Genet.* 227:229-237 and Gatz et al. (1994) *Mol. Gen. Genetics* 243:32-38); the maize GST promoter, which is activated by hydrophobic electrophilic compounds that are used as pre-emergent herbicides; the tobacco PR-1a promoter, which is activated by salicylic acid; and Tet repressor from Tn10 (Gatz et al. 1991) *Mol. Gen. Genet.* 227:229-237). A particularly preferred inducible promoter is a promoter that responds to an inducing agent to which plants do not normally respond. Exemplary promoters are steroid-responsive promoters (see, for example, the glucocorticoid-inducible promoter in Schena et al. (1991) *Proc. Natl. Acad. Sci. USA* 88:10421-10425 and McNellis et al. (1998) *Plant J.* 14(2):247-257) and tetracycline-inducible promoters (see, for example, Gatz et al. (1991) *Mol. Gen. Genet.* 227:229-237, and U.S. Pat. Nos. 5,814,618 and 5,789,156), herein incorporated by reference.

Tissue-preferred promoters can be utilized to drive expression of inhibitory RNA transcripts within a particular plant tissue. Tissue-preferred promoters can be utilized to target enhanced expression within a particular plant tissue. Tissue-preferred promoters include Yamamoto et al. (1997) *Plant J.* 12(2):255-265; Kawamata et al. (1997) *Plant Cell Physiol.* 38(7):792-803; Hansen et al. (1997) *Mol. Gen. Genet.* 254 (3):337-343; Russell et al. (1997) *Transgenic Res.* 6(2):157-168; Rinehart et al. (1996) *Plant Physiol.* 112(3):1331-1341; Van Camp et al. (1996) *Plant Physiol.* 112(2):525-535; Canevascini et al. (1996) *Plant Physiol.* 112(2):513-524; Yamamoto et al. (1994) *Plant Cell Physiol.* 35(5):773-778; Lam (1994) *Results Probl. Cell Differ.* 20:181-196; Orozco et al. (1993) *Plant Mol Biol.* 23(6):1129-1138; Matsuoka et al. (1993) *Proc Natl. Acad. Sci. USA* 90(20):9586-9590; and Guevara-Garcia et al. (1993) *Plant J.* 4(3):495-505. Such promoters can be modified, if necessary, for weak expression.

Leaf-preferred promoters are known in the art. See, for example, Yamamoto et al. (1997) *Plant J.* 12(2):255-265; Kwon et al. (1994) *Plant Physiol.* 105:357-67; Yamamoto et al. (1994) *Plant Cell Physiol.* 35(5):773-778; Gotor et al. (1993) *Plant J.* 3:509-18; Orozco et al. (1993) *Plant Mol. Biol.* 23(6):1129-1138; and Matsuoka et al. (1993) *Proc. Natl. Acad. Sci. USA* 90(20):9586-9590.

Root-preferred promoters are known in the art and can be selected from the many available from the literature or isolated de novo from various compatible species. See, for example, Hire et al. (1992) *Plant Mol. Biol.* 20(2):207-218 (soybean root-preferred glutamine synthetase gene); Keller and Baumgartner (1991) *Plant Cell* 3(10):1051-1061 (root-preferred control element in the GRP 1.8 gene of French bean); Sanger et al. (1990) *Plant Mol. Biol.* 14(3):433-443 (root-preferred promoter of the mannopine synthase (MAS) gene of *Agrobacterium tumefaciens*); and Miao et al. (1991) *Plant Cell* 3(1):11-22 (full-length cDNA clone encoding cytosolic glutamine synthetase (GS), which is expressed in roots and root nodules of soybean). See also Bogusz et al. (1990) *Plant Cell* 2(7):633-641, where two root-preferred promoters isolated from hemoglobin genes from the nitrogen-fixing nonlegume *Parasponia andersonii* and the related non-nitrogen-fixing nonlegume *Trema tomentosa* are described. The promoters of these genes were linked to a β-glucuronidase reporter gene and introduced into both the nonlegume *Nicotiana tabacum* and the legume *Lotus corniculatus*, and in both instances root-preferred promoter activity was preserved. Leach and Aoyagi (1991) describe their analysis of the promoters of the highly expressed rolC and rolD root-inducing genes of *Agrobacterium rhizogenes* (see *Plant Science* (Limerick) 79(1):69-76). They concluded that enhancer and tissue-preferred DNA determinants are dissociated in those promoters. Teeri et al. (1989) used gene fusion to lacZ to show that the *Agrobacterium* T-DNA gene encoding octopine synthase is especially active in the epidermis of the root tip and that the TR2' gene is root specific in the intact plant and stimulated by wounding in leaf tissue, an especially desirable combination of characteristics for use with an insecticidal or larvicidal gene (see *EMBO J.* 8(2):343-350). The TR1' gene, fused to nptII (neomycin phosphotransferase II) showed similar characteristics. Additional root-preferred promoters include the VfENOD-GRP3 gene promoter (Kuster et al. (1995) *Plant Mol. Biol.* 29(4):759-772); and rolB promoter (Capana et al. (1994) *Plant Mol. Biol.* 25(4):681-691). See also U.S. Pat. Nos. 5,837,876; 5,750,386; 5,633,363; 5,459,252; 5,401,836; 5,110,732; and 5,023,179.

"Seed-preferred" promoters include both "seed-specific" promoters (those promoters active during seed development such as promoters of seed storage proteins) as well as "seed-germinating" promoters (those promoters active during seed germination). See Thompson et al. (1989) *BioEssays* 10:108, herein incorporated by reference. For dicots, seed-preferred promoters include, but are not limited to promoters for the phaseolin seed storage proteins (for example, bean β-phaseolin promoter; see Riggs (1989) *Plant Sci.* 63:47-57; Bustos et al. (1991) *EMBO J.* 10:1469-1479), the napin promoter (see, for example, Radke et al. (1988) *Theor. Appl. Genet.* 75:685-694; Kohno-Murase et al. (1994) *Plant Mol. Biol.* 26:1115-1124), β-conglycinin promoter (see, for example, Lessard et al, (1991) *Plant Mol. Biol.* 16:379-413), soybean lectin promoter (see, for example, Okamura et al. (1986) *Proc. Natl. Acad. Sci. USA* 83:8240-8244), glabra2 promoter (see Cameron et al. (2002) *Plant Cell* 14:1359-1375, and *Arabidopsis thaliana* glabra2 promoter deposited as GenBank Accession No. L32873), 12S cruciferin seed storage protein promoter (see *Arabidopsis thaliana* ATCRU3 gene deposited in GenBank as Accession No. 66916), cruciferin promoter (see *Brassica napus* cruciferin promoter deposited as GenBank Accession No. M16860), the KTI promoters (see, US Application Publication No. 20040073975 and Jofuku et al. (1989) *Plant Cell* 1:1079-1093), oleosin promoters (see *Brassica juncea* oleosin promoter deposited as GenBank Accession No. AF134411, *Glycine max* oleosin promoter deposited as GenBank Accession No. U71381, and *Arabidopsis thaliana* oleosin promoter disclosed in U.S. Pat. No. 5,977,436; see also Plant et al. (1994) *Plant Mol. Biol.* 25:193-205 (*Arabadopsis thaliana* oleosin promoter); Keddie et al. (1994) *Plant Mol. Biol.* 24:327-40 and Keddie et al. (1992) *Plant Mol. Biol.* 19:443-53 (*Brassica napus* oleosin promoter)), and the like. Paricarp-preferred promoters include promoters such as the LTP1 promoter. See, for example, WO 95/23230, herein incorporated by reference.

For monocots, such seed-preferred promoters include, but are not limited to, maize 15 kDa zein promoter, 22 kDa zein promoter, 27 kDa zein promoter (see the sequence deposited as GenBank Accession No. X58197), gamma-zein promoter (gzw64A); also see the sequence deposited as GenBank Accession No. S78780), mze40-2 promoter from maize (see U.S. Pat. No. 6,403,862), b22e promoter from barley (see Klemsdal et al. (1991) Mol. Gen. Genetics 228:9-16), waxy promoter, shrunken 1 and shrunken 2 promoters (see, for example, Shaw et al. (1992) Plant. Physiol. 98:1214-1216, and Zhong Chen et al. (2003) Proc. Natl. Acad. Sci. USA 100:3525-3530), globulin 1 (glb1) promoter (see the *Zea mays* promoter deposited as GenBank Accession No. L22344), oleosin promoters (see, for example, *Zea mays* L3 oleosin promoter (PZmL3) disclosed in Hong et al. (1997) Plant Mol. Biol. 34:549-555), lipid transfer protein 2 (LTP2) promoters (for example, rice LTP2 promoter disclosed in Morino et al. (1999) Plant J. 17:275-285, barley LTP2 promoter disclosed in U.S. Pat. No. 5,525,716 and Kalla et al. (1994) Plant J. 6:849-860, and maize LTP2 promoter disclosed in International Publication No. WO 00/11177), nucl promoter (see U.S. Pat. No. 6,407,315), Zm40 promoter (see U.S. Pat. No. 6,403,862), mlip 15 promoter (see U.S. Pat. No. 6,479,734), Led promoter (for example, maize Led promoter, SEQ ID NO:9 of U.S. Patent Application Publication No. 20040237147—now U.S. Pat. No. 7,531,723), maize end1 and end2 promoters (see U.S. Pat. No. 6,528,704; International Patent Publication No. WO 00/12733; and U.S. patent application Ser. No. 10/310,191, filed Dec. 4, 2002 (now U.S. Pat. No. 6,903,205), eep1 (SEQ ID NO:7 of U.S. Patent Application Publication No. 20040237147—now U.S. Pat. No. 7,531,723) and eep2 (SEQ ID NO:18 of U.S. Patent Application Publication No. 20040237147—now U.S. Pat. No. 7,531,723); PCNA2 promoter (SEQ ID NO:25 of U.S. Patent Application Publication No. 20040237147—now U.S. Pat. No. 7,531,723); thioredoxinH promoter (SEQ ID NO: 19 of U.S. Patent Application Publication No. 20040237147— now U.S. Pat. No. 7,531,723); the nucellain promoter (see Linnestad et al. (1998) Plant Physiol. 118:1169-80); the knl promoter (see Hake and Ori, Keystone Symposia, Feb. 8-14, 1999, Abstract B8 at 27), the F3.7 promoter (SEQ ID N0:10 of U.S. Patent Application Publication No. 20040237147— now U.S. Pat. No. 7,531,723; see also Baszczynski et al. (1997) Maydica 42:189); the BETL1 promoter (see Hueros et al. (1999) Plant Physiol. 121:1143-1152 and Hueros et al. (1995) Plant Cell 7:747-57); Ciml (cytokinin-induced message, which expresses in nucellus tissue; see U.S. Pat. No. 6,225,529, describing the *Zea mays* Ciml promoter); cZ19BI (maize 19 kDa zein; see U.S. Pat. No. 6,225,529); milps (myo-inositol-1—phosphate synthase; see WO 00/11177 and U.S. Pat. No. 6,225,529; herein incorporated by reference); EAP1 (early abundant protein 1; see U.S. Patent Application Publication No. 20040210043); rita-1 promoter from rice (Izawa et al. (1994) Plant Cell 6:1277-1287); *Zea mays* Opaque-2 promoter (Gallusci et al. (1994) Mol. Gen. Genetics 244:391-400; Kirihara et al. (1988) Mol. Gen. Genetics 211:477-484; Kirihara et al. (1988) Gene 71:359-370); cytokinin oxidase promoters (for example, ZmCkx2, ZmCkx3, ZmCkx4, and ZmCkxS promoters set forth as SEQ ID NO:34, 35, 36, and 37, respectively, of U.S. Patent Application Publication No. 20040237147—now U.S. Pat. No. 7,531,723); and the GLB2 promoter or biologically active variants or fragments thereof (SEQ ID NO:2).

Anther-specific promoters can also be used and include, for example, a tapetum-specific promoter such as the tobacco anther promoter, ant32, an anther-specific promoter such as that from LAT52 (Twell et al. (1989) *Mol. Gen. Genet.* 217: 240-245, and the anther specific promoter 5126 (U.S. Pat. Nos. 5,689,049 and 5,689,051). Another anther-specific promoter includes the MS45 promoter. See, U.S. Application Publication No. 2004/0221331, herein incorporated by reference. Pollen-preferred promoters include, for example, the Zm13 promoter (Guerrero et al. (1993) Mol. Gen. Genet. 224: 161-168), and the SF3 promoter (U.S. Pat. No. 6,452,069). See, also, Guerrero (1990) *Mol. Gen. Genet.* 224:161-168.

The convergent promoters can be chosen to provide for spatially different expression profiles, for example, within the same plant part such as a seed. In the same manner, the promoters may be chosen to provide temporally different expression profiles within the same plant part, such as seed. For example, the glb1, oleosin, and EAP1 promoters provide for expression in an embryo-preferred manner while the gamma-zein, rita-1, and Opaque-2 promoters provide for expression in an endosperm-preferred manner. The LTP2, EN2 and b22e promoters provide for expression preferentially in the aleurone. The Cim1 and nuc1 promoters provide for expression preferentially in the nucellus. The end1 and BETL1 promoters provide for expression preferentially in endosperm transfer cells. Other such promoters include a promoter active in the embryo-surrounding region (ESR) (see U.S. Patent Application Publication No. 20040210960), promoters that are preferentially active in female reproductive tissues, and those that are active in meristematic tissues, particularly in meristematic female reproductive tissues. Thus, by using selective promoters, careful regulation of a target polynucleotide can be controlled.

Likewise, promoters can be selected to provide somewhat precise temporal control of expression. In this manner, for example, seed-preferred promoters that act from 0-25 days after pollination (DAP) are useful, as are those acting from 4-21, 4-12, or 8-12 days DAP. Such promoters include cim1, LTP2, nuc1, b22e, end1, and BETL1. Other promoters that act from −14 to 0 DAP include SAG12 (see WO 96/29858) and ZAG1 or ZAG2 (see Schmidt et al. (1993) *Plant Cell*

5(7):729-37 and SEQ ID NO:3 of U.S. Patent Application Publication No. 20040237147). Other useful promoters that can provide temporal expression patterns include, but are not limited to, zap (SEQ ID NO:5 of U.S. Patent Application Publication No. 20040237147 also known as ZmMADS; see also International Patent Application Publication No. WO 03/078590); maize tb1 promoter (SEQ ID NO:17 of U.S. Patent Application Publication No. 20040237147; see also Hubbarda et al. (2002) *Genetics* 162:1927-1935); and ODP1, oleosin, maize end2, eep1, eep2, and lec1 promoters.

Senescence promoters may be selected to confer temporal regulation of genes in specific tissues including promoters for senescence-induced receptor-like kinase (SIRK), senescence-associated receptor-like kinase (SARK), WRKY6, and WRKY DNA-binding protein 53 (WRKY53); the senescence-associated gene (SAG12; see, for example, U.S. Pat. Nos. 5,689,042, 6,359,197, and WO 96/29858, maize lethal leaf-spot 1 (LLS-1) promoters (see, for example, U.S. Pat. No. 6,818,806).

Thus, depending on the desired results any combination of convergent promoters can be used. While it is recognized that two identical promoters could be used in the suppression cassette or different promoter having the same expression profile, in specific embodiments, the convergent promoters will have differential expression profiles.

In still other embodiments, the suppression cassette comprises two recombination sites which flank at least one of the silencing elements and are internal to the convergent promoters. In this embodiment, the recombination sites can be used to allow for efficient exchange of the silencing element. See, for example, WO99/25821, WO99/25854, WO99/25840, WO99/25855, and WO99/25853, all of which are herein incorporated by reference.

A "decreased level" or "decreasing the level" of a polynucleotide or a polypeptide in the context of the methods of the present invention refers to any decrease in the expression, concentration, and/or activity of a gene product (i.e., polypeptide or polynucleotide), including any relative increment in expression, concentration and/or activity. The term "expression" as used herein in the context of a gene product, refers to the biosynthesis of that product including the transcription or translation of the gene product. In general, the level of the polypeptide or the polynucleotide is decreased by at least 1%, 5%, 10%, 20%, 30%, 40%, 50%, 60%, 70%, 80%, 90%, 95%, or greater relative to a native control plant, plant part, or cell. The expression level of the gene product of interest may be measured directly, for example, by assaying for the level of that gene product expressed in the plant or plant part thereof, or indirectly, for example, by measuring the activity of the gene product in the plant or plant part thereof using assays specific for the gene product of interest. The "decrease level" may occur during and/or subsequent to growth of the plant to the desired stage of development. In specific embodiments, the polynucleotides or the polypeptides of the present invention are modulated in monocots, particularly maize.

A "subject plant or plant cell" is one in which genetic alteration, such as transformation, has been affected as to a polynucleotide of interest, or is a plant or plant cell which is descended from a plant or cell so altered and which comprises the alteration. A "control" or "control plant" or "control plant cell" provides a reference point for measuring changes in phenotype of the subject plant or plant cell.

A control plant or plant cell may comprise, for example: (a) a wild-type plant or cell, i.e., of the same genotype as the starting material for the genetic alteration which resulted in the subject plant or cell; (b) a plant or plant cell of the same genotype as the starting material but which has been transformed with a null construct (i.e. with a construct which has no known effect on the trait of interest, such as a construct comprising a marker gene); (c) a plant or plant cell which is a non-transformed segregant among progeny of a subject plant or plant cell; (d) a plant or plant cell genetically identical to the subject plant or plant cell but which is not exposed to conditions or stimuli that would induce expression of the gene of interest; or (e) the subject plant or plant cell itself, under conditions in which the gene of interest is not expressed.

The expression of the silencing elements of the invention can be used for example, to impart commercially important agronomic traits in plants, such as improved grain quality, improved feed value including more balanced amino acids and/or higher available energy, and improved wet milling characteristics including higher oil and/or reduced fiber. In mammals, the methods of the invention can be used to treat or prevent diseases or disease states.

The suppression cassettes of the present invention can be used to target any polynucleotide of interest or combination of polynucleotides wherein a decrease of expression of the polynucleotide provides for a desirable phenotypic change in the host organism. In this manner, the silencing element within the suppression cassette is designed such that the encoded hairpin RNA transcripts target one or more polynucleotides of interest including any cellular RNA (such as, but not limited to, an endogenous RNA, a viral RNA, an RNA transcribed from introduced vectors such as plasmids, an RNA transcribed from a transgene, and the like).

Target polynucleotides of interest include polynucleotides involved in primary and secondary biosynthetic pathways. Thus, for example, where the host organism is a plant, the polynucleotide targeted for suppression can be involved in amino acid and protein biosynthesis; nucleic acid biosynthesis; mineral nutrient uptake and transport; nitrogen and sulfur metabolism; photosynthesis and carbohydrate metabolism; cell wall biosynthesis; fatty acid metabolism; membrane biosynthesis; membrane transport processes; hormone biosynthesis; cytoskeleton biosynthesis; and the like. Other genes of interest include, but are not limited to, those involved in biotic and abiotic stress responses; those involved in signal perception; those involved in developmental processes such as vegetative and reproductive growth, dormancy, and senescence and programmed death; those involved in secondary metabolism; for example, biosynthesis of alkaloids, terpenoids, and phenylpropanoids; and the like. In some embodiments, the host organism is a plant and the polynucleotides of interest include those involved in fatty acid metabolism.

In one embodiment, the suppression cassette of the invention can be used to alter cell wall biosynthesis. For example, it is known that down regulating hemicellulose biosynthesis increases the digestibility of feed. Hemicellulose includes such sugars as xylan, glucuronoxylan, arabinoxylan, glucomannan, and xyloglucan. One of the enzymes involved in hemicellulose biosynthesis via the arabinose synthetic pathway is reversibly glycosylated polypeptide-1 (RGP1). See for example, the *Arabidopsis thalania* nucleotide sequence deposited as GenBank Accession No. AF013627, Delgado et al. (1998) *Plant Physiol.* 116:1339-1350, Langeveld et al. (2002) *Plant Physiol.* 129:278-289, and U.S. Pat. No. 6,194,638; the *Gossypium hirsutum* (upland cotton) sequence deposited as GenBank Accession No. AJ292078; and the maize RGP1 nucleotide sequence set forth in U.S. Pat. No. 6,194,638; each of these references is herein incorporated by reference in their entirety. In other embodiments, the USX gene is targeted for down regulation. See, for example, U.S. Provisional Application No. 60/755,253, herein incorporated by reference in its entirety.

As shown herein, suppressing the expression of RGP1 in a seed-preferred manner decreases hemicellulose and arabinose biosynthesis. Suppression cassette that provide for expression of RNA transcripts that inhibit RGP1 (i.e., RGP1 inhibitory transcripts) are described herein and include constructs expressing RNA transcripts that form stem-loop structures, such as constructs comprising the sequence set forth in SEQ ID NO:2 and described herein below in Example 1. The present suppression cassette is advantageous as it provides an efficient means to inhibit RGP1 expression in spatially separated tissues within a seed, for example, within the endosperm (i.e., with a gamma-zein or Opaque-2 promoter) and the embryo (i.e., with a globulin 1, oleosin, or EAP1 promoter), and can provide for expression of the inhibitory RNA transcripts throughout early and late seed development. See, for example, FIG. 1 and FIG. 2 which illustrate embodiments wherein inhibition of hemicellulose was targeted in both the embryo and endosperm of the transformed seed by using the oleosin promoter and the gamma-zein promoter. In other embodiments, one member of the convergent promoter pair drives expression of the RGP1 inhibitory RNA transcript during early seed development, for example, the eep1 or eep2 promoter, and the other member is a promoter that drives expression of the RGP1 inhibitory RNA transcript during late seed development, for example, an oleosin promoter. Use of these suppression cassette in the methods of the present invention can provide for decreased hemicellulose and/or arabinose content in the seed or part thereof, for example, endosperm and embryo, and/or throughout early and late seed development.

In yet other embodiments of the invention, phytic acid biosynthesis can be manipulated. Phytic acid (myo-inositol-1,2,3,4,5,6-hexakisphosphate; Ins P6) can comprise between 50% to 80% of the phosphorus in plant seeds. In maize (*Zea mays*) kernels, nearly 90% of the phytic acid accumulates in the embryo, with only about 10% accumulating in the aleurone layer, and only trace amounts being found in the endosperm (O'Dell et al. (1972) *J. Agric. Food. Chem.* 20:718-721). In rice (*Oryza sativa*), barley (*Hordeum vulgare*), and wheat (*Triticum aestivum*), most of the phytic acid (approximately 90%) is found in the aleurone layer and only about 10% accumulates in the embryo. In view of the poor digestibility of phytic acid, the diet of monogastric animals must be supplemented with inorganic phosphate (Pi) to meet their phosphorus requirement. Poor digestibility also results in phytic acid release into the environment, contributing to phosphorus pollution (Cromwell and Coffey (1991) in *Biotechnology in the Feed Industry*, ed. Lyons (Alltech Tech Publishers, Nicholasville, Ky.), pp. 133-145). In view of these and other problems associated with phytic acid, reduced phytic acid content in seeds is a desired goal for genetic improvement in several crops, including maize, rice, barley, wheat, and soybean (*Glycine max*). The down regulation of phytic acid biosynthesis can increase the digestibility of feed, decrease the amount of phosphorus supplementation required in animal feeds (Ertl et al. (1998) *J. Environ. Qual.* 27:299-304), and reduce phosphorus pollution into the environment. Reducing the phytic acid levels also improves grain wet milling characteristics by reducing phytic acid precipitation during the milling process (Pen et al. (1993) *Bio/Tech.* 11:811). Low-phytic acid mutants have been generated by mutagenesis in maize, rice, barley, and soybean (Rasmussen and Hatzack (1998) *Hereditas* 129:107-112); Larson et al. (2000) *Crop. Sci.* 40:1397-1405); Raboy et al. (2000) *Plant Physiol.* 124:355-368); Wilcox et al. (2000) *Crop. Sci.* 40:1601-1605). Seeds of the low phytic acid mutants lpa1-1 and lpa1-2 have phytic acid levels that are reduced over 55% relative to wild-type maize seed. See Raboy et al. (2000) *Plant Physiol.* 124:355-368, U.S. Pat. No. 6,111,168, and U.S. Pat. No. 5,689,054. The recombinant constructs of the present invention provide an alternative efficient method for generating transformed plants that produce seed having a low-phytic acid content.

Thus, by transforming a plant with an expression construct of the invention that targets one or more genes involved in the phytic acid biosynthesis pathway, phytic acid production in the plant seed can be decreased throughout seed development or in the particular seed tissues of interest. Genes involved in phytic acid biosynthesis are known in the art. Examples include, but are not limited to, the maize inositol phosphate kinase gene ZmIpk (see coding sequence disclosed in Shi et al. (2003) *Plant Physiol.* 131:507-515), in which Mu insertions account for the maize lpa2 mutant phenotype; genes involved in the maize lpa1 mutant phenotype (see Raboy et al. (2000) *Plant Physiol.* 124:355-368, and U.S. Pat. Nos. 5,689,054 and 6,111,168); genes encoding inositol polyphosphate kinases such as those disclosed in U.S. Patent Application Publication No. 20030009011; other genes implicated in phytic acid metabolic pathways such as myo-inositol 1-phosphate synthase (MI1PS) (see for example *Glycine max* MI1PS deposited in GenBank as Accession No. AY038802), inositol 1,3,4-trisphosphate 5/6 kinases (ITPKs) and myo-inositol monophosphatase (IMP) (see U.S. Patent Application Publication No. 20030079247), and the like; the disclosures of which are herein incorporated by reference in their entirety.

As noted, the suppression cassettes of the invention can be used to inhibit the expression of target polynucleotides of interest. Expression of any given polynucleotide of interest in a genetically modified plant or plant part thereof is decreased if the transcript level or the protein level, for example, of RGP1, AGP, or FAD, is statistically lower than the transcript level or the protein level in a control plant.

The expression level of a polypeptide and/or an RNA may be measured directly, for example, by assaying for the level of the polypeptide or the RNA in the plant, or indirectly, for example, by measuring the activity of the polypeptide or the RNA in the plant. For example, the level of RGP1 can be assayed using methods disclosed herein below. Inhibiting the expression of any given gene product of interest may occur during and/or subsequent to growth of the plant to the desired stage of development.

The use of the term "polynucleotide" is not intended to limit the present invention to polynucleotides comprising DNA. Those of ordinary skill in the art will recognize that polynucleotides, can comprise ribonucleotides and combinations of ribonucleotides and deoxyribonucleotides. Such deoxyribonucleotides and ribonucleotides include both naturally occurring molecules and synthetic analogues. The polynucleotides of the invention also encompass all forms of sequences including, but not limited to, single-stranded forms, double-stranded forms, hairpins, stem-and-loop structures, and the like.

The suppression cassettes of the invention are introduced into cells of interest, for example, plant cells, mammalian cells, and the like. Subsequently, a cell having the construct of the invention is selected using methods known to those of skill in the art such as, but not limited to, Southern blot analysis, DNA sequencing, PCR analysis, or phenotypic analysis. A cell altered or modified by the foregoing embodiments is grown or propagated under the proper conditions for a time sufficient to reduce the concentration and/or activity of target RNA and polypeptides.

The suppression constructs can be constructed on vectors or DNA constructs comprising additional cassettes designed to express selectable markers, other genes of interest, and the like. Alternatively, additional gene(s) can be provided on multiple constructs. Such constructs are provided with a plurality of restriction sites and/or recombination sites for insertion of a polynucleotide to be under the transcriptional regulation of a regulatory region. The regulatory regions (e.g., promoters, transcriptional regulatory regions, and translational termination regions, including those within the cassette and/or the polynucleotide of interest may be native/analogous to the host cell or to each other. Alternatively, the regulatory regions and/or the polynucleotide of interest may be heterologous to the host cell or to each other. As used herein, "heterologous" in reference to a sequence is a sequence that originates from a foreign species, or, if from the same species, is substantially modified from its native form in composition and/or genomic locus by deliberate human intervention. For example, a heterologous promoter operably linked to a polynucleotide of interest is from a species different from the species from which the promoter was derived, or, if from the same/analogous species, one or both are substantially modified from their original form and/or genomic locus, or the promoter is not the native promoter for the operably linked polynucleotide.

In preparing DNA constructs, various DNA fragments may be manipulated, so as to provide for DNA sequences in the proper orientation and, as appropriate, in the proper reading frame. Toward this end, adapters or linkers may be employed to join DNA fragments or other manipulations may be involved to provide for convenient restriction sites, removal of superfluous DNA, removal of restriction sites, or the like. For this purpose, in vitro mutagenesis, primer repair, restriction, annealing, resubstitutions, e.g., transitions and transversions, may be involved.

In certain embodiments, a suppression cassette comprising a silencing element of the invention can be "stacked" with any combination of polynucleotide of interest in order to create an organism, more particularly plants, with a desired phenotype. By "stacked" or "stacking" is intended that an organism, for example, a plant of interest, contains one or more nucleic acids collectively comprising multiple polynucleotides so that the transcription and/or expression of multiple polynucleotides are altered in the organism.

In this manner, a suppression cassette comprising the silencing elements as disclosed herein can be stacked with any other polynucleotide(s) to produce plants having a variety of desired trait combinations including, for example, traits desirable for animal feed such as high oil genes (see, e.g., U.S. Pat. No. 6,232,529, which is incorporated herein by reference); balanced amino acids (e.g., hordothionins; see U.S. Pat. Nos. 5,990,389; 5,885,801; 5,885,802; and 5,703,409, each of which is incorporated herein by reference); barley high lysine (Williamson et al. (1987) *Eur. J. Biochem.* 165: 99-106, WO 98/20122 and WO 98/20133); high methionine proteins (Pedersen et al. (1986) *J. Biol. Chem.* 261: 6279; Kirihara et al. (1988) *Gene* 71: 359; and Musumura et al. (1989) *Plant Mol. Biol.* 12: 123); increased digestibility (e.g., modified storage proteins) and thioredoxins (U.S. Ser. No. 10/005,429, filed Dec. 3, 2001).

Suppression cassettes of the invention can also be stacked with one or more polynucleotides encoding a desirable trait such as a polynucleotide that confers, for example, insect, disease or herbicide resistance (e.g., *Bacillus thuringiensis* toxic proteins; U.S. Pat. Nos. 5,366,892; 5,747,450; 5,737,514; 5,723,756; 5,593,881; Geiser et al. (1986) *Gene* 48: 109); lectins (Van Damme et al. (1994) *Plant Mol. Biol.* 24: 825); fumonisin detoxification genes (U.S. Pat. No. 5,792,931); avirulence and disease resistance genes (Jones et al. (1994) *Science* 266: 789; Martin et al. (1993) *Science* 262: 1432; Mindrinos et al. (1994) *Cell* 78: 1089); acetolactate synthase mutants that lead to herbicide resistance such as the S4 and/or Hra mutations; inhibitors of glutamine synthase such as phosphinothricin or basta (e.g., the bar gene); and glyphosate resistance (EPSPS gene). Additional polynucleotides that can be stacked include, for example, those encoding traits desirable for processing or process products such as modified oils (e.g., fatty acid desaturase genes (U.S. Pat. No. 5,952,544; WO 94/11516); modified starches (e.g., AGPases, starch synthases, starch branching enzymes, and starch debranching enzymes); modified cell wall amounts and/or properties (e.g., UDP-glucose dehydrogenase (U.S. Pat. No. 6,399,859), Reversibly Glycosylated Polypeptide (RGP1) (see the *Arabidopsis thalania* nucleotide sequence deposited as GenBank Accession No. AF013627, Delgado et al. (1998) *Plant Physiol.* 116:1339-1350, Langeveld et al. (2002) *Plant Physiol.* 129:278-289, and U.S. Pat. No. 6,194,638; and the *Gossypium hirsutum* (upland cotton) sequence deposited as GenBank Accession No. AJ292078)); and polymers or bioplastics (e.g., U.S. Pat. No. 5,602,321). Recombinant constructs comprising a suppression cassette can be stacked with one or more polynucleotides that provide desirable agronomic traits such as male sterility (e.g., U.S. Pat. No. 5,583,210), stalk strength, flowering time, or transformation technology traits such as cell cycle regulation or gene targeting (e.g., WO 99/61619; WO 00/17364; WO 99/25821). Other desirable traits that are known in the art include high oil content; increased digestibility; balanced amino acid content; and high energy content. Such traits may refer to properties of both seed and non-seed plant tissues, or to food or feed prepared from plants or seeds having such traits.

These stacked combinations can be created by any method including but not limited to cross breeding plants. If traits are stacked by genetically transforming the plants, the nucleic acids of interest can be combined at any time and in any order. Similarly, where a method requires more than one step to be performed, it is understood that steps may be performed in any order that accomplishes the desired end result. For example, a transgenic plant comprising one or more desired traits can be used as the target to introduce further traits by subsequent transformation. The traits can be introduced simultaneously in a co-transformation protocol with the polynucleotides of interest provided by any combination of cassettes suitable for transformation. For example, if two sequences will be introduced, the two sequences can be contained in separate cassettes (trans) or contained on the same transformation cassette (cis). Transcription and/or expression of the sequences can be driven by the same promoter or by different promoters. In specific embodiments, the promoters of the suppression cassette are chosen to provide for differential profile expressions. Alternatively, traits may be stacked by transforming different plants to obtain those traits; the transformed plants may then be crossed together and progeny may be selected which contains all of the desired traits.

The methods of the invention involve introducing a polynucleotide into a plant. "Introducing" is intended to mean presenting to the plant the polynucleotide in such a manner that the sequence gains access to the interior of a cell of the plant. The methods of the invention do not depend on a particular method for introducing a sequence into a plant, only that the polynucleotide gains access to the interior of at least one cell of the plant. Methods for introducing polynucleotides into plants are known in the art including, but not limited to, stable transformation methods, transient transformation methods, and virus-mediated methods.

"Stable transformation" is intended to mean that the nucleotide construct introduced into a plant integrates into the genome of the plant and is capable of being inherited by the progeny thereof. "Transient transformation" is intended to mean that a polynucleotide is introduced into the plant and does not integrate into the genome of the plant.

Transformation protocols as well as protocols for introducing polynucleotide sequences into plants may vary depending on the type of plant or plant cell, i.e., monocot or dicot, targeted for transformation. Suitable methods of introducing polynucleotides into plant cells include microinjection (Crossway et al. (1986) *Biotechniques* 4:320-334), electroporation (Riggs et al. (1986) *Proc. Natl. Acad. Sci. USA* 83:5602-5606, *Agrobacterium*-mediated transformation (U.S. Pat. No. 5,563,055 and U.S. Pat. No. 5,981,840), direct gene transfer (Paszkowski et al. (1984) *EMBO J.* 3:2717-2722), and ballistic particle acceleration (see, for example, U.S. Pat. No. 4,945,050; U.S. Pat. No. 5,879,918; U.S. Pat. Nos. 5,886,244; and 5,932,782; Tomes et al. (1995) in *Plant Cell, Tissue, and Organ Culture: Fundamental Methods*, ed. Gamborg and Phillips (Springer-Verlag, Berlin); McCabe et al. (1988) *Biotechnology* 6:923-926); and Lec1 transformation (WO 00/28058). Also see Weissinger et al. (1988) *Ann. Rev. Genet.* 22:421-477; Sanford et al. (1987) *Particulate Science and Technology* 5:27-37 (onion); Christou et al. (1988) *Plant Physiol.* 87:671-674 (soybean); McCabe et al. (1988) *Biotechnology* 6:923-926 (soybean); Finer and McMullen (1991) *In Vitro Cell Dev. Biol.* 27P:175-182 (soybean); Singh et al. (1998) *Theor. Appl. Genet.* 96:319-324 (soybean); Datta et al. (1990) *Biotechnology* 8:736-740 (rice); Klein et al. (1988) *Proc. Natl. Acad. Sci. USA* 85:4305-4309 (maize); Klein et al. (1988) *Biotechnology* 6:559-563 (maize); U.S. Pat. Nos. 5,240,855; 5,322,783; and, 5,324,646; Klein et al. (1988) *Plant Physiol.* 91:440-444 (maize); Fromm et al. (1990) *Biotechnology* 8:833-839 (maize); Hooykaas-Van Slogteren et al. (1984) *Nature (London)* 311:763-764; U.S. Pat. No. 5,736,369 (cereals); Bytebier et al. (1987) *Proc. Natl. Acad. Sci. USA* 84:5345-5349 (Liliaceae); De Wet et al. (1985) in *The Experimental Manipulation of Ovule Tissues*, ed. Chapman et al. (Longman, N.Y.), pp. 197-209 (pollen); Kaeppler et al. (1990) *Plant Cell Rep.* 9:415-418 and Kaeppler et al. (1992) *Theor. Appl. Genet.* 84:560-566 (whisker-mediated transformation); D'Halluin et al. (1992) *Plant Cell* 4:1495-1505 (electroporation); Li et al. (1993) *Plant Cell Rep.* 12:250-255 and Christou and Ford (1995) *Ann. Bot.* 75:407-413 (rice); Osjoda et al. (1996) *Nat. Biotechnol.* 14:745-750 (maize via *Agrobacterium tumefaciens*); all of which are herein incorporated by reference.

In specific embodiments, the suppression cassettes of the invention can be provided to a plant using a variety of transient transformation methods. Such methods include, for example, microinjection or particle bombardment. See, for example, Crossway et al. (1986) *Mol. Gen. Genet.* 202:179-185; Nomura et al. (1986) *Plant Sci.* 44:53-58; Hepler et al. (1994) *Proc. Natl. Acad. Sci. USA* 91: 2176-2180 and Hush et al. (1994) *J. of Cell Sci.* 107:775-784, all of which are herein incorporated by reference. Alternatively, the recombinant constructs comprising the suppression cassettes can be transiently transformed into the plant using techniques known in the art. Such techniques include viral vector system and the precipitation of the polynucleotide in a manner that precludes subsequent release of the DNA. Thus, the transcription from the particle-bound DNA can occur, but the frequency with which it is released to become integrated into the genome is greatly reduced. Such methods include the use of particles coated with polyethylimine (PEI; Sigma #P3143).

In other embodiments, the recombinant constructs of the invention may be introduced into plants by contacting plants with a virus or viral nucleic acids. Generally, such methods involve incorporating a recombinant construct of the invention within a viral DNA or RNA molecule. Further, it is recognized that promoters of the invention also encompass promoters utilized for transcription by viral RNA polymerases. Methods for introducing polynucleotides into plants and expressing a transcript encoded therein, involving viral DNA or RNA molecules, are known in the art. See, for example, U.S. Pat. Nos. 5,889,191; 5,889,190; 5,866,785; 5,589,367; 5,316,931, and Porta et al. (1996) *Mol. Biotechnol.* 5:209-221; herein incorporated by reference.

Methods are known in the art for the targeted insertion of a polynucleotide at a specific location in the plant genome. In one embodiment, the insertion of a recombinant construct comprising the suppression cassette at a desired genomic location is achieved using a site-specific recombination system. See, for example, International Publication Nos. WO99/25821, WO99/25854, WO99/25840, WO99/25855, and WO99/25853, all of which are herein incorporated by reference. Briefly, the suppression cassette can be contained in a transfer cassette flanked by two non-recombinogenic recombination sites. The transfer cassette is introduced into a plant having stably incorporated into its genome a target site which is flanked by two non-recombinogenic recombination sites that correspond to the sites of the transfer cassette. An appropriate recombinase is provided and the transfer cassette is integrated at the target site. The suppression cassette is thereby integrated at a specific chromosomal position in the plant genome.

Where the suppression cassette of the invention have been introduced into plant cells, the transformed plant cells may be grown into plants in accordance with conventional ways. See, for example, McCormick et al. (1986) *Plant Cell Rep.* 5:81-84. These plants may then be grown, and either pollinated with the same transformed strain or different strains, and the resulting progeny having the desired phenotypic characteristic identified. Two or more generations may be grown to ensure that expression of the desired phenotypic characteristic is stably maintained and inherited and then seeds harvested to ensure expression of the desired phenotypic characteristic has been achieved. In this manner, the present invention provides transformed seed (also referred to as "transgenic seed") having a suppression cassette of the invention stably incorporated into their genome.

In specific embodiments, the transformants will have a desired phenotype such as a change in oil content of the plant, a change in the starch content, a change in the phytic acid content, a change in hemicellulose content, combinations thereof, and the like upon transcription of the suppression cassette of interest in a plant. These transformed plants find use in the wet milling industry. In the wet milling process, the purpose is to fractionate the kernel and isolate chemical constituents of economic value into their component parts. The process allows for the fractionation of starch into a highly purified form, as well as for the isolation in crude forms of other material including, for example, unrefined oil, or as a wide mix of materials that commonly receive little to no additional processing beyond drying. Hence, in the wet milling process, grain is softened by steeping and cracked by grinding to release the germ from the kernels. The germ is separated from the heavier density mixture of starch, hulls, and fiber by "floating" the germ segments free of the other substances in a centrifugation process. This allows a clean separation of the oil-bearing fraction of the grain from tissue fragments that contain the bulk of the starch. As it is not economical to extract oil on a small scale, many wet milling plants ship their germ to large, centralized oil production facilities. Oil is expelled or extracted with solvents from dried germs and the remaining germ meal is commonly mixed into corn gluten feed (CGF), a coproduct of wet milling. Hence, starch contained within the germ is not recovered as such in the wet milling process and is channeled to CGF. See, for example, Anderson et al. (1982) "*The Corn Milling Industry*"; *CRC Handbook of Processing and Utilization in Agriculture*, A. Wolff, Boca Raton, Fla., CRC Press., Inc., Vol. 11, Part 1, *Plant Products:* 31-61 and Eckhoff (Jun. 24-26, 1992) *Proceedings of the 4th Corn Utilization Conference*, St. Louis, Mo., printed by the National Corn Growers Association, CIBA-GEIGY Seed Division, and the USDA, both of which are herein incorporated by reference.

As used herein, the term "plant" includes plant cells, plant protoplasts, plant cell tissue cultures from which maize plant can be regenerated, plant calli, plant clumps, and plant cells that are intact in plants or parts of plants such as embryos, pollen, ovules, seeds, leaves, flowers, branches, fruit, kernels, ears, cobs, husks, stalks, roots, root tips, anthers, and the like. Grain is intended to mean the mature seed produced by commercial growers for purposes other than growing or reproducing the species. Progeny, variants, and mutants of the regenerated plants are also included within the scope of the invention, provided that these parts comprise the introduced polynucleotides.

The present invention may be used for transformation of any plant species, including, but not limited to, monocots and dicots. Examples of plant species of interest include, but are not limited to, corn (*Zea mays*), *Brassica* sp. (e.g., *B. napus, B. rapa, B. juncea*), particularly those *Brassica* species useful as sources of seed oil, alfalfa (*Medicago sativa*), rice (*Oryza sativa*), rye (*Secale cereale*), sorghum (*Sorghum bicolor, Sorghum vulgare*), millet (e.g., pearl millet (*Pennisetum glaucum*), proso millet (*Panicum miliaceum*), foxtail millet (*Setaria italica*), finger millet (*Eleusine coracana*), sunflower (*Helianthus annuus*), safflower (*Carthamus tinctorius*), wheat (*Triticum aestivum*), soybean (*Glycine max*), tobacco (*Nicotiana tabacum*), potato (*Solanum tuberosum*), peanuts (*Arachis hypogaea*), cotton (*Gossypium barbadense, Gossypium hirsutum*), sweet potato (*Ipomoea batatus*), cassava (*Manihot esculenta*), coffee (*Coffea* spp.), coconut (*Cocos nucifora*), pineapple (*Ananas comosus*), citrus trees (*Citrus* spp.), cocoa (*Theobroma cacao*), tea (*Camellia sinensis*), banana (*Musa* spp.), avocado (*Persea americana*), fig (*Ficus casica*), guava (*Psidium guajava*), mango (*Mangifera indica*), olive (*Olea europaea*), papaya (*Carica papaya*), cashew (*Anacardium occidentale*), macadamia (*Macadamia integrifolia*), almond (*Prunus amygdalus*), sugar beets (*Beta vulgaris*), sugarcane (*Saccharum* spp.), oats, barley, vegetables, ornamentals, and conifers.

Vegetables include tomatoes (*Lycopersicon esculentum*), lettuce (e.g., *Lactuca sativa*), green beans (*Phaseolus vulgaris*), lima beans (*Phaseolus limensis*), peas (*Lathyrus* spp.), and members of the genus *Cucumis* such as cucumber (*C. sativus*), cantaloupe (*C. cantalupensis*), and musk melon (*C. melo*). Ornamentals include azalea (*Rhododendron* spp.), hydrangea (*Macrophylla hydrangea*), hibiscus (*Hibiscus rosasanensis*), roses (*Rosa* spp.), tulips (*Tulipa* spp.), daffodils (*Narcissus* spp.), petunias (*Petunia hybrida*), carnation (*Dianthus caryophyllus*), poinsettia (*Euphorbia pulcherrima*), and chrysanthemum.

Conifers that may be employed in practicing the present invention include, for example, pines such as loblolly pine (*Pinus taeda*), slash pine (*Pinus elliotii*), ponderosa pine (*Pinus ponderosa*), odgepole pine (*Pinus contorta*), and Monterey pine (*Pinus radiata*), Douglas-fir (*Pseudotsuga menziesii*), Western hemlock (*Tsuga canadensis*), Sitka spruce (*Picea glauca*), redwood (*Sequoia sempervirens*), true firs such as silver fir (*Abies amabilis*) and balsam fir (*Abies balsamea*), and cedars such as Western red cedar (*Thuja plicata*) and Alaska yellow-cedar (*Chamaecyparis nootkatensis*). In specific embodiments, plants of the present invention are crop plants (for example, corn, alfalfa, sunflower, *Brassica*, soybean, cotton, safflower, peanut, sorghum, wheat, millet, tobacco, etc.). In other embodiments, corn and soybean plants are optimal, and in yet other embodiments corn plants are optimal.

II. Glb2 Promoter Sequences and Variants Thereof and Methods of Use

The invention further relates to compositions and methods drawn to plant promoters and methods of their use. The compositions comprise polynucleotides for the promoter of the Mr 45,000 globulin component (Glb2) gene. The compositions further comprise DNA constructs comprising a nucleotide sequence for the promoter region of the Glb2 gene operably linked to a heterologous nucleotide sequence of interest. In particular, the present invention provides for isolated polynucleotides comprising the nucleotide sequence set forth in SEQ ID NO:3.

The Gbl2 promoter sequences of the present invention include polynucleotide constructs that allow initiation of transcription in a plant. In specific embodiments, the Gbl2 promoter sequence allows initiation of transcription in a tissue-preferred, more particularly in an embryo-preferred manner. In specific embodiments, the Gbl2 promoter sequence allows initiation of transcription in the embryo at 20 DAP through 34 DAP. Thus, the compositions of the present invention comprise novel plant promoter polynucleotides, particularly embryo-preferred promoter sequences for the Gbl2 gene, more particularly a maize Gbl2 promoter sequence. The sequence for the maize Gbl2 promoter region is set forth in SEQ ID NO:3.

Compositions of the invention include the nucleotide sequences for the native Gbl2 promoter and fragments and variants thereof. The promoter sequences of the invention are useful for expressing sequences. In specific embodiments, the promoter sequences of the invention are useful for expressing sequences of interest in a tissue-preferred, particularly an embryo-preferred manner. The sequences of the invention also find use in the construction of expression vectors for subsequent expression of a heterologous nucleotide sequence in a plant of interest or as probes for the isolation of other Gbl2-like promoters.

The invention encompasses isolated or substantially purified nucleic acid compositions. An "isolated" or "purified" nucleic acid molecule or biologically active portion thereof, is substantially free of other cellular material, or culture medium when produced by recombinant techniques, or substantially free of chemical precursors or other chemicals when chemically synthesized. An "isolated" nucleic acid is free of sequences (optimally protein encoding sequences) that naturally flank the nucleic acid (i.e., sequences located at the 5' and 3' ends of the nucleic acid) in the genomic DNA of the organism from which the nucleic acid is derived. For example, in various embodiments, the isolated nucleic acid molecule can contain less than about 5 kb, 4 kb, 3 kb, 2 kb, 1 kb, 0.5 kb, or 0.1 kb of nucleotide sequences that naturally flank the nucleic acid molecule in genomic DNA of the cell from which the nucleic acid is derived. The Gbl2 promoter sequences of the invention may be isolated from the 5' untranslated region flanking their respective transcription initiation sites.

Fragments and variants of the disclosed promoter sequences are also encompassed by the present invention. In particular, fragments and variants of the Gbl2 promoter sequence of SEQ ID NO:3 may be used in the DNA constructs of the invention. As used herein, the term "fragment" means a portion of the nucleic acid sequence. Fragments of a Gbl2 promoter sequence may retain the biological activity of initiating transcription. Alternatively, fragments of a nucleotide sequence that is useful as hybridization probes may not necessarily retain biological activity. Fragments of a nucleotide sequence for the promoter region of the Gbl2 gene may range from at least about 20 nucleotides, about 30 nucleotides, about 40 nucleotides, about 50 nucleotides, about 60 nucleotides, about 70 nucleotides, about 80 nucleotides, about 90 nucleotides, about 100 nucleotides, about 150 nucleotides, about 175 nucleotides, and up to the full-length nucleotide sequence of the invention for the promoter region of the gene.

A biologically active portion of a Gbl2 promoter can be prepared by isolating a portion of the Gbl2 promoter sequence of the invention, and assessing the promoter activity of the fragment. Polynucleotides that are fragments of a Gbl2 promoter nucleotide sequence comprise at least about 16, 20, 40, 50, 65, 75, 80, 90, 100, 125, 150, 175, 200, 225, 250, 275, 300, 350, 400, 450, 500, 550, 600, 650 nucleotides, or up to the number of nucleotides present in a full-length Gbl2 promoter sequence disclosed herein.

As used herein, the term "variants" means substantially similar sequences. For nucleotide sequences, naturally occurring variants can be identified with the use of well-known molecular biology techniques, such as, for example, with polymerase chain reaction (PCR) and hybridization techniques as outlined herein. For nucleotide sequences, a variant comprises a deletion and/or addition of one or more nucleotides at one or more internal sites within the native polynucleotide and/or a substitution of one or more nucleotides at one or more sites in the native polynucleotide. As used herein, a "native" nucleotide sequence comprises a naturally occurring nucleotide sequence. For nucleotide sequences, naturally occurring variants can be identified with the use of well-known molecular biology techniques, as, for example, with polymerase chain reaction (PCR) and hybridization techniques as outlined below. Variant nucleotide sequences also include synthetically derived nucleotide sequences, such as those generated, for example, by using site-directed mutagenesis. Generally, variants of a particular nucleotide sequence of the invention will have at least about 40%, 45%, 50%, 55%, 60%, 65%, 70%, 75%, 80%, 85%, 90%, 91%, 92%, 93%, 94%, 95%, 96%, 97%, 98%, 99% or more sequence identity to that particular nucleotide sequence as determined by sequence alignment programs and parameters described elsewhere herein. A biologically active variant of a nucleotide sequence of the invention may differ from that sequence by as few as 1-15 nucleic acid residues, as few as 1-10, such as 6-10, as few as 5, as few as 4, 3, 2, or even 1 nucleic acid residue.

Variant polynucleotides also encompass sequences derived from a mutagenic and recombinogenic procedure such as DNA shuffling. With such a procedure, one or more different Gbl2 nucleotide sequences for the promoter can be manipulated to create a new Gbl2 promoter. In this manner, libraries of recombinant polynucleotides are generated from a population of related sequence polynucleotides comprising sequence regions that have substantial sequence identity and can be homologously recombined in vitro or in vivo. Strategies for such DNA shuffling are known in the art. See, for example, Stemmer (1994) *Proc. Natl. Acad. Sci. USA* 91:10747-10751; Stemmer (1994) *Nature* 370:389-391; Crameri et al. (1997) *Nature Biotech.* 15:436-438; Moore et al. (1997) *J. Mol. Biol.* 272:336-347; Zhang et al. (1997) *Proc. Natl. Acad. Sci. USA* 94:4504-4509; Crameri et al. (1998) *Nature* 391:288-291; and U.S. Pat. Nos. 5,605,793 and 5,837,458.

The nucleotide sequences of the invention can be used to isolate corresponding sequences from other organisms, particularly other plants, more particularly other monocots. In this manner, methods such as PCR, hybridization, and the like can be used to identify such sequences based on their sequence homology to the sequences set forth herein. Sequences isolated based on their sequence identity to the entire Gbl2 sequences set forth herein or to fragments thereof are encompassed by the present invention.

In a PCR approach, oligonucleotide primers can be designed for use in PCR reactions to amplify corresponding DNA sequences from genomic DNA extracted from any plant of interest. Methods for designing PCR primers and PCR cloning are generally known in the art and are disclosed in Sambrook et al. (1989) *Molecular Cloning: A Laboratory Manual* (2d ed., Cold Spring Harbor Laboratory Press, Plainview, N.Y.), hereinafter Sambrook. See also Innis et al., eds. (1990) *PCR Protocols: A Guide to Methods and Applications* (Academic Press, New York); Innis and Gelfand, eds. (1995) *PCR Strategies* (Academic Press, New York); and Innis and Gelfand, eds. (1999) *PCR Methods Manual* (Academic Press, New York). Known methods of PCR include, but are not limited to, methods using paired primers, nested primers, single specific primers, degenerate primers, gene-specific primers, vector-specific primers, partially-mismatched primers, and the like.

In hybridization techniques, all or part of a known nucleotide sequence is used as a probe that selectively hybridizes to other corresponding nucleotide sequences present in a population of cloned genomic DNA fragments from a chosen organism. The hybridization probes may be labeled with a detectable group such as $^{32}$P, or any other detectable marker. Thus, for example, probes for hybridization can be made by labeling synthetic oligonucleotides based on the Gbl2 promoter sequences of the invention. Methods for preparation of probes for hybridization and for construction of genomic libraries are generally known in the art and are disclosed in Sambrook.

For example, the entire Gbl2 promoter sequence disclosed herein, or one or more portions thereof, may be used as a probe capable of specifically hybridizing to corresponding Gbl2 promoter sequences and messenger RNAs. To achieve specific hybridization under a variety of conditions, such probes include sequences that are unique among Gbl2 promoter sequences and are at least about 10 nucleotides in length or at least about 20 nucleotides in length. Such probes may be used to amplify corresponding Gbl2 promoter sequences from a chosen plant by PCR. This technique may be used to isolate additional coding sequences from a desired organism or as a diagnostic assay to determine the presence of coding sequences in an organism. Hybridization techniques include hybridization screening of plated DNA libraries (either plaques or colonies; see, for example, Sambrook et al. (1989) *Cloning: A Laboratory Manual* (2$^{nd}$ ed, Cold Spring Harbor Laboratory Press, Plainview, N.Y.)

Hybridization of such sequences may be carried out under stringent conditions. The terms "stringent conditions" and "stringent hybridization conditions" are intended to mean conditions under which a probe will hybridize to its target sequence to a detectably greater degree than to other sequences (e.g., at least 2-fold over background). Stringent conditions are sequence-dependent and will be different in different circumstances. By controlling the stringency of the hybridization and/or washing conditions, target sequences that are 100% complementary to the probe can be identified (homologous probing). Alternatively, stringency conditions can be adjusted to allow some mismatching in sequences so that lower degrees of similarity are detected (heterologous probing). Generally, a probe is less than about 1000 nucleotides in length or less than 500 nucleotides in length.

Typically, stringent conditions will be those in which the salt concentration is less than about 1.5 M Na ion, typically about 0.01 to 1.0 M Na ion concentration (or other salts) at pH 7.0 to 8.3 and the temperature is at least about 30° C. for short probes (e.g., 10 to 50 nucleotides) and at least about 60° C. for long probes (e.g., greater than 50 nucleotides). Stringent conditions may also be achieved with the addition of destabilizing agents such as formamide. Exemplary low stringency conditions include hybridization with a buffer solution of 30 to 35% formamide, 1 M NaCl, 1% SDS (sodium dodecyl sulphate) at 37° C., and a wash in 1× to 2×SSC (20×SSC=3.0 M NaCl/0.3 M trisodium citrate) at 50 to 55° C. Exemplary moderate stringency conditions include hybridization in 40 to 45% formamide, 1.0 M NaCl, 1% SDS at 37° C., and a wash in 0.5× to 1×SSC at 55 to 60° C. Exemplary high stringency conditions include hybridization in 50% formamide, 1 M NaCl, 1% SDS at 37° C., and a final wash in 0.1×SSC at 60 to 65° C. for a duration of at least 30 minutes. Duration of hybridization is generally less than about 24 hours, usually about 4 to about 12 hours. The duration of the wash time will be at least a length of time sufficient to reach equilibrium.

Specificity is typically the function of post-hybridization washes, the critical factors being the ionic strength and temperature of the final wash solution. For DNA-DNA hybrids, the $T_m$ (thermal melting point) can be approximated from the equation of Meinkoth and Wahl (1984) *Anal. Biochem.* 138: 267-284: $T_m = 81.5°$ C.$+16.6(\log M)+0.41(\% GC)-0.61(\% form)-500/L$; where M is the molarity of monovalent cations, % GC is the percentage of guanosine and cytosine nucleotides in the DNA, % form is the percentage of formamide in the hybridization solution, and L is the length of the hybrid in base pairs. The $T_m$ is the temperature (under defined ionic strength and pH) at which 50% of a complementary target sequence hybridizes to a perfectly matched probe. $T_m$ is reduced by about 1° C. for each 1% of mismatching; thus, $T_m$, hybridization, and/or wash conditions can be adjusted to hybridize to sequences of the desired identity. For example, if sequences with ≥90% identity are sought, the $T_m$ can be decreased 10° C. Generally, stringent conditions are selected to be about 5° C. lower than the $T_m$ for the specific sequence and its complement at a defined ionic strength and pH. However, severely stringent conditions can utilize a hybridization and/or wash at 1, 2, 3, or 4° C. lower than the $T_m$; moderately stringent conditions can utilize a hybridization and/or wash at 6, 7, 8, 9, or 10° C. lower than the $T_m$; low stringency conditions can utilize a hybridization and/or wash at 11, 12, 13, 14, 15, or 20° C. lower than the $T_m$. Using the equation, hybridization and wash compositions, and desired $T_m$, those of ordinary skill will understand that variations in the stringency of hybridization and/or wash solutions are inherently described. If the desired degree of mismatching results in a $T_m$ of less than 45° C. (aqueous solution) or 32° C. (formamide solution), it is preferred to increase the SSC concentration so that a higher temperature can be used. An extensive guide to the hybridization of nucleic acids is found in Tijssen (1993) *Laboratory Techniques in Biochemistry and Molecular Biology—Hybridization with Nucleic Acid Probes*, Part I, Chapter 2 (Elsevier, N.Y.); and Ausubel et al., eds. (1995) *Current Protocols in Molecular Biology*, Chapter 2 (Greene Publishing and Wiley-Interscience, New York). See also Sambrook.

Thus, isolated sequences that have embryo-preferred promoter activity and which hybridize under stringent conditions to the Gbl2 promoter sequences disclosed herein, or to fragments thereof, are encompassed by the present invention. Generally, stringent conditions are selected to be about 5° C. lower than the $T_m$ for the specific sequence at a defined ionic strength and pH. However, stringent conditions encompass temperatures in the range of about 1° C. to about 20° C. lower than the $T_m$, depending upon the desired degree of stringency as otherwise qualified herein.

Heterologous coding sequences expressed by the Gbl2 promoters of the invention may be used for varying the phenotype of a plant. Various changes in phenotype are of interest including modifying expression of a gene in a plant embryo, altering a plant's pathogen or insect defense mechanism, increasing the plants tolerance to herbicides in a plant, altering embryo development to respond to environmental stress, and the like. These results can be achieved by the expression of a heterologous nucleotide sequence of interest comprising an appropriate gene product. In specific embodiments, the heterologous nucleotide sequence of interest is an endogenous plant sequence whose expression level is increased in the plant or plant part, such as the embryo. Alternatively, the results can be achieved by providing for a reduction of expression of one or more endogenous gene products, particularly enzymes, transporters, or cofactors. These changes can result in a change in phenotype of the transformed plant.

General categories of polynucleotides of interest for the present invention include, for example, those genes involved in information, such as zinc fingers, those involved in communication, such as kinases, and those involved in housekeeping, such as heat shock proteins. More specific categories of transgenes, for example, include genes encoding important traits for agronomics, insect resistance, disease resistance, herbicide resistance, and environmental stress resistance (altered tolerance to cold, salt, drought, etc). It is recognized that any gene of interest can be operably linked to the promoter of the invention and expressed in the plant.

Insect resistance genes may encode resistance to pests that have great yield drag such as rootworm, cutworm, European corn borer, and the like. Such genes include, for example, *Bacillus thuringiensis* toxic protein genes (U.S. Pat. Nos. 5,366,892; 5,747,450; 5,736,514; 5,723,756; 5,593,881; and Geiser et al. (1986) *Gene* 48:109); and the like.

Genes encoding disease resistance traits include detoxification genes, such as those which detoxify fumonisin (U.S. Pat. No. 5,792,931); avirulence (avr) and disease resistance (R) genes (Jones et al. (1994) *Science* 266:789; Martin et al. (1993) *Science* 262:1432; and Mindrinos et al. (1994) *Cell* 78:1089); and the like.

Herbicide resistance traits may include genes coding for resistance to herbicides that act to inhibit the action of acetolactate synthase (ALS), in particular the sulfonylurea-type herbicides (e.g., the acetolactate synthase (ALS) gene containing mutations leading to such resistance, in particular the S4 and/or Hra mutations), genes coding for resistance to herbicides that act to inhibit action of glutamine synthase, such as phosphinothricin or basta (e.g., the bar gene), glyphosate (e.g., the EPSPS gene and the GAT gene; see, for example, U.S. Publication No. 20040082770 and WO 03/092360) or other such genes known in the art. The bar gene encodes resistance to the herbicide basta, the nptII gene encodes resistance to the antibiotics kanamycin and geneticin, and the ALS gene mutants encode resistance to the herbicide chlorsulfuron.

Glyphosate resistance is imparted by mutant 5-enolpyruvl-3-phosphikimate synthase (EPSP) and aroA genes. See, for example, U.S. Pat. No. 4,940,835 to Shah et al., which discloses the nucleotide sequence of a form of EPSPS which can confer glyphosate resistance. U.S. Pat. No. 5,627,061 to Barry et al. also describes genes encoding EPSPS enzymes. See also U.S. Pat. Nos. 6,248,876 B1; 6,040,497; 5,804,425; 5,633,435; 5,145,783; 4,971,908; 5,312,910; 5,188,642; 4,940,835; 5,866,775; 6,225,114 BI; 6,130,366; 5,310,667; 4,535,060; 4,769,061; 5,633,448; 5,510,471; Re. 36,449; RE 37,287 E; and 5,491,288; and international publications WO 97/04103; WO 97/04114; WO 00/66746; WO 01/66704; WO 00/66747 and WO 00/66748, which are incorporated herein by reference for this purpose. Glyphosate resistance is also imparted to plants that express a gene that encodes a glyphosate oxidoreductase enzyme as described more fully in U.S. Pat. Nos. 5,776,760 and 5,463,175, which are incorporated herein by reference for this purpose. In addition glyphosate resistance can be imparted to plants by the over expression of genes encoding glyphosate N-acetyltransferase. See, for example, U.S. patent application Ser. No. 10/004,357 (now, US Application Publication No. 2003-0083480); and Ser. No. 10/427,692 (Now U.S. Pat. No. 7,462,481).

Exogenous products include plant enzymes and products as well as those from other sources including prokaryotes and other eukaryotes. Such products include enzymes, cofactors, hormones, and the like.

Examples of other applicable genes and their associated phenotype include the gene which encodes viral coat protein and/or RNA, or other viral or plant genes that confer viral resistance; genes that confer fungal resistance; genes that promote yield improvement; and genes that provide for resistance to stress, such as cold, dehydration resulting from drought, heat and salinity, toxic metal or trace elements, or the like.

As noted, the heterologous polynucleotide operably linked to the Gbl2 promoters disclosed herein may be an antisense sequence for a targeted gene. Thus the promoter sequences disclosed herein may be operably linked to antisense DNA sequences to reduce or inhibit expression of a native protein in the plant embryo.

"RNAi" refers to a series of related techniques to reduce the expression of genes (See for example U.S. Pat. No. 6,506,559). Older techniques referred to by other names are now thought to rely on the same mechanism, but are given different names in the literature. These include "antisense inhibition," the production of antisense RNA transcripts capable of suppressing the expression of the target protein, and "co-suppression" or "sense-suppression," which refer to the production of sense RNA transcripts capable of suppressing the expression of identical or substantially similar foreign or endogenous genes (U.S. Pat. No. 5,231,020, incorporated herein by reference). Such techniques rely on the use of constructs resulting in the accumulation of double stranded RNA with one strand complementary to the target gene to be silenced. The Gbl2 promoters of the embodiments may be used to drive expression of constructs that will result in RNA interference including microRNAs and siRNAs.

The term "promoter" or "transcriptional initiation region" is intended to mean a regulatory region of DNA usually comprising a TATA box capable of directing RNA polymerase II to initiate RNA synthesis at the appropriate transcription initiation site for a particular coding sequence. A promoter may additionally comprise other recognition sequences generally positioned upstream or 5' to the TATA box, referred to as upstream promoter elements, which influence the transcription initiation rate. It is recognized that having identified the nucleotide sequences for the promoter regions disclosed herein, it is within the state of the art to isolate and identify further regulatory elements in the 5' untranslated region upstream from the particular promoter regions identified herein. Additionally, chimeric promoters may be provided. Such chimeras include portions of the promoter sequence fused to fragments and/or variants of heterologous transcriptional regulatory regions. Thus, the promoter regions disclosed herein can comprise upstream regulatory elements such as, those responsible for tissue and temporal expression of the coding sequence, enhancers and the like. In the same manner, the promoter elements, which enable expression in the desired tissue, such as the embryo, can be identified, isolated and used with other core promoters to confer embryo-preferred expression. In this aspect of the invention, a "core promoter" is intended to mean a promoter without promoter elements.

In the context of this disclosure, the term "regulatory element" also refers to a sequence of DNA, usually, but not always, upstream (5') to the coding sequence of a structural gene, which includes sequences which control the expression of the coding region by providing the recognition for RNA polymerase and/or other factors required for transcription to start at a particular site. An example of a regulatory element that provides for the recognition for RNA polymerase or other transcriptional factors to ensure initiation at a particular site is a promoter element. A promoter element comprises a core promoter element, responsible for the initiation of transcription, as well as other regulatory elements (as discussed elsewhere in this application) that modify gene expression. It is to be understood that nucleotide sequences, located within introns, or 3' of the coding region sequence may also contribute to the regulation of expression of a coding region of interest. Examples of suitable introns include, but are not limited to, the maize IVS6 intron, or the maize actin intron. A regulatory element may also include those elements located downstream (3') to the site of transcription initiation, or within transcribed regions, or both. In the context of the present invention a post-transcriptional regulatory element may include elements that are active following transcription initiation, for example translational and transcriptional enhancers, translational and transcriptional repressors, and mRNA stability determinants.

The regulatory elements, or variants or fragments thereof, of the present invention may be operatively associated with heterologous regulatory elements or promoters in order to modulate the activity of the heterologous regulatory element. Such modulation includes enhancing or repressing transcriptional activity of the heterologous regulatory element, modulating post-transcriptional events, or either enhancing or repressing transcriptional activity of the heterologous regulatory element, and modulating post-transcriptional events. For example, one or more regulatory elements, or fragments thereof, of the present invention may be operatively associated with constitutive, inducible, or tissue-specific promoters or fragment thereof, to modulate the activity of such promoters within desired tissues in plant cells.

The regulatory sequences of the present invention, or variants or fragments thereof, when operably linked to a heterologous nucleotide sequence of interest can drive embryo-preferred expression of the heterologous nucleotide sequence in the embryo of the plant expressing this construct. The term "embryo-preferred" is intended to mean that expression of the heterologous nucleotide sequence is most abundant in the embryo or a part of the embryo, While some level of expression of the heterologous nucleotide sequence may occur in other plant tissue types, expression occurs most abundantly in the embryo or embryo part.

A "heterologous polynucleotide" is intended to mean a sequence that is not naturally occurring with the promoter sequence of the invention. While this nucleotide sequence is heterologous to the promoter sequence, it may be homologous, or native, or heterologous, or foreign, to the plant host.

The isolated promoter sequences of the present invention can be modified to provide for a range of expression levels of the heterologous polynucleotide. Thus, less than the entire promoter regions may be utilized and the ability to drive expression of the nucleic acid sequence of interest retained. It is recognized that expression levels of the mRNA may be altered in different ways by deletions of portions of the promoter sequences. The mRNA expression levels may be decreased, or alternatively, expression may be increased as a result of promoter deletions if, for example, there is a negative regulatory element (for a repressor) that is removed during the truncation process. Generally, at least about 20 nucleotides of an isolated promoter sequence will be used to drive expression of a nucleotide sequence.

It is recognized that to increase transcription levels, enhancers may be utilized in combination with the promoter regions of the invention. Enhancers are nucleotide sequences that act to increase the expression of a promoter region. Enhancers are known in the art and include the SV40 enhancer region, the 35S enhancer element, and the like. Some enhancers are also known to alter normal promoter expression patterns, for example, by causing a promoter to be expressed constitutively when without the enhancer, the same promoter is expressed only in one specific tissue or a few specific tissues.

Modifications of the isolated promoter sequences of the present invention can provide for a range of expression of the heterologous nucleotide sequence. Thus, they may be modified to be weak promoters or strong promoters. Generally, a "weak promoter" is intended to mean a promoter that drives expression of a coding sequence at a low level. A "low level" of expression is intended to mean expression at levels of about 1/10,000 transcripts to about 1/100,000 transcripts to about 1/500,000 transcripts. Conversely, a strong promoter drives expression of a coding sequence at a high level, or at about 1/10 transcripts to about 1/100 transcripts to about 1/1,000 transcripts.

It is recognized that the promoters of the invention may be used with their native Gbl2 coding sequences to increase or decrease expression, thereby resulting in a change in phenotype of the transformed plant. This phenotypic change could further affect an increase or decrease in levels of metal ions in tissues of the transformed plant.

The nucleotide sequences disclosed in the present invention, as well as, variants and fragments thereof, are useful in the genetic manipulation of any plant. The Gbl2 promoter sequences are useful in this aspect when operably linked with a heterologous nucleotide sequence whose expression is to be controlled to achieve a desired phenotypic response. In this manner, the nucleotide sequences for the promoters of the invention may be provided in expression cassettes along with heterologous nucleotide sequences of interest for expression in the plant of interest, more particularly in the embryo of the plant.

Such expression cassettes will comprise a transcriptional initiation region comprising one of the promoter nucleotide sequences of the present invention, or variants or fragments thereof, operably linked to the heterologous nucleotide sequence. Such an expression cassette can be provided with a plurality of restriction sites for insertion of the nucleotide sequence to be under the transcriptional regulation of the regulatory regions. The expression cassette may additionally contain selectable marker genes as well as 3' termination regions.

The expression cassette can include, in the 5'-3' direction of transcription, a transcriptional initiation region (i.e., a promoter, or variant or fragment thereof, of the invention), a translational initiation region, a heterologous nucleotide sequence of interest, a translational termination region and, optionally, a transcriptional termination region functional in the host organism. The regulatory regions (i.e., promoters, transcriptional regulatory regions, and translational termination regions) and/or the polynucleotide of the embodiments may be native/analogous to the host cell or to each other. Alternatively, the regulatory regions and/or the polynucleotide of the embodiments may be heterologous to the host cell or to each other.

While it may be preferable to express a heterologous nucleotide sequence using the promoters of the invention, the native sequences may be expressed. Such constructs would change expression levels of the Gbl2 protein in the plant or plant cell. Thus, the phenotype of the plant or plant cell can be altered.

The termination region may be native with the transcriptional initiation region, may be native with the operably linked DNA sequence of interest, may be native with the plant host, or may be derived from another source (i.e., foreign or heterologous to the promoter, the DNA sequence being expressed, the plant host, or any combination thereof). Exemplary termination sequences are discussed elsewhere herein.

The expression cassette comprising the sequences of the present invention may also contain at least one additional nucleotide sequence for a gene to be cotransformed into the organism. Alternatively, the additional sequence(s) can be provided on another expression cassette.

The expression cassettes may additionally contain 5' leader sequences. Such leader sequences can act to enhance translation. Translation leaders are known in the art and include: picornavirus leaders, for example, EMCV leader (Encephalomyocarditis 5' noncoding region) (Elroy-Stein et al. (1989) *Proc. Nat. Acad. Sci. USA* 86:6126-6130); potyvirus leaders, for example, TEV leader (Tobacco Etch Virus) (Allison et al. (1986) *Virology* 154:9-20)); MDMV leader (Maize Dwarf Mosaic Virus); human immunoglobulin heavy-chain binding protein (BiP) (Macejak et al. (1991) *Nature* 353:90-94); untranslated leader from the coat protein mRNA of alfalfa mosaic virus (AMV RNA 4) (Jobling et al. (1987) *Nature* 325:622-625); tobacco mosaic virus leader (TMV) (Gallie et al. (1989) *Molecular Biology of RNA*, pages 237-256); and maize chlorotic mottle virus leader (MCMV) (Lommel et al. (1991) *Virology* 81:382-385). See also Della-Cioppa et al. (1987) *Plant Physiology* 84:965-968. Methods known to enhance mRNA stability can also be utilized, for example, introns, such as the maize Ubiquitin intron (Christensen and Quail (1996) *Transgenic Res.* 5:213-218; Christensen et al. (1992) *Plant Molecular Biology* 18:675-689) or the maize AdhI intron (Kyozuka et al. (1991) *Mol. Gen. Genet.* 228:40-48; Kyozuka et al. (1990) *Maydica* 35:353-357), and the like.

Reporter genes or selectable marker genes may be included in the expression cassettes. Examples of suitable reporter genes known in the art can be found in, for example, Jefferson et al. (1991) in *Plant Molecular Biology Manual*, ed. Gelvin et al. (Kluwer Academic Publishers), pp. 1-33; DeWet et al. (1987) *Mol. Cell. Biol.* 7:725-737; Goff et al. (1990) *EMBO J.*

9:2517-2522; Kain et al. (1995) *BioTechniques* 19:650-655; and Chiu et al. (1996) *Current Biology* 6:325-330.

The expression cassette comprising the Gb12 promoter of the present invention, operably linked to a polynucleotide of interest, can be used to transform any plant. In this manner, genetically modified plants, plant cells, plant tissue, seed, embryos, and the like can be obtained.

The following examples are offered by way of illustration and not by way of limitation.

EXPERIMENTAL

Example 1

Suppression Cassette Provides for Differential Promoter Expression of Reversibly Glycosylated Polypeptide-1 (RGP1)

Figure 2:
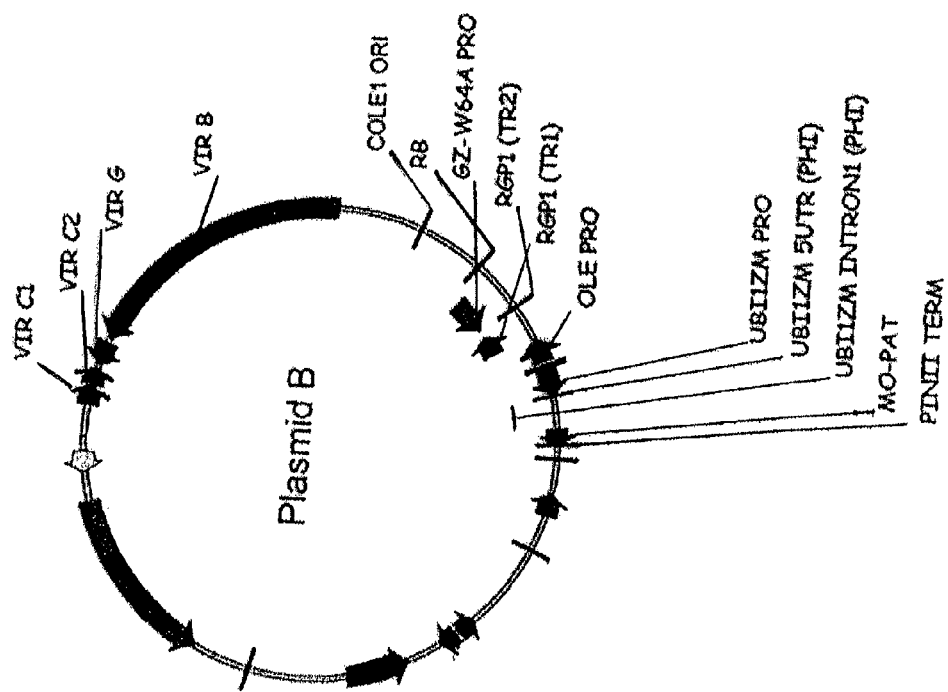
FIG. 2 depicts a vir integrated plasmid (Plasmid B) comprising the suppression cassette shown in FIG. 1.

The maize RGP1 gene encodes a polypeptide that is involved in hemicellulose production (see, for example, U.S. Pat. No. 6,194,638, herein incorporated by reference in its entirety). An inverted repeat comprising a sense and antisense sequence of the maize RGP1 gene was created using standard molecular biology protocols. A 277 base pair (bp) HindIII-ApaI fragment from the 5' end of the RGP1 coding sequence was ligated into a cloning intermediate. This plasmid was restriction digested, the end filled in with Klenow enzyme, and then digested with a second restriction enzyme. Into this backbone, a second fragment of RGP1 (an 848 bp BamHI/HpaI fragment, also from the 5' end of the coding sequence) was ligated, such that the second fragment was in reverse orientation relative to the first fragment. The suppression cassette was created by moving the promoter from the maize 16 kDa oleosin gene (OLE PRO; a BamHI/BglII fragment (969 bp)) into a cloning intermediate vector. From this, the OLE PRO was moved as a 997 bp HpaI/HindIII fragment into a GZ-W64A PRO cassette (from the maize 27 kDa gamma-zein gene), replacing the GZ-W64A terminator sequence. The resulting vector comprised the two promoters directed toward each other, separated by a multi-cloning site. The RGP1 inverted repeat fragment was ligated as a 1129 bp BamHI fragment into BglII-digested plasmid. The entire promoter:inverted repeat:promoter cassette (SEQ ID NO:1) was finally moved as a BstEII fragment into a BstEII-digested binary vector (Plasmid A; FIG. 1). This plasmid was transferred by electroporation into electro-competent *Agrobacterium tumefaciens* cells, where cos-specific recombination with a resident vir plasmid resulted in the formation of a cointegrate plasmid (Plasmid B, FIG. 2). Immature embryos of maize (GS3×HG69) were transformed using *Agrobacterium tumefaciens* cells carrying Plasmid B.

Hemicellulose Assay
Seed Dissection

Nineteen mature kernels from each transformation event were soaked overnight in water at 4° C. The seeds were cut in half and dissected into embryo and endosperm. The dissected embryo and endosperm were dried in a lyophilizer. One-half of each endosperm or embryo was used for Western blotting and the remaining half was used for hemicellulose analysis.

Western Blots

Figure 3:
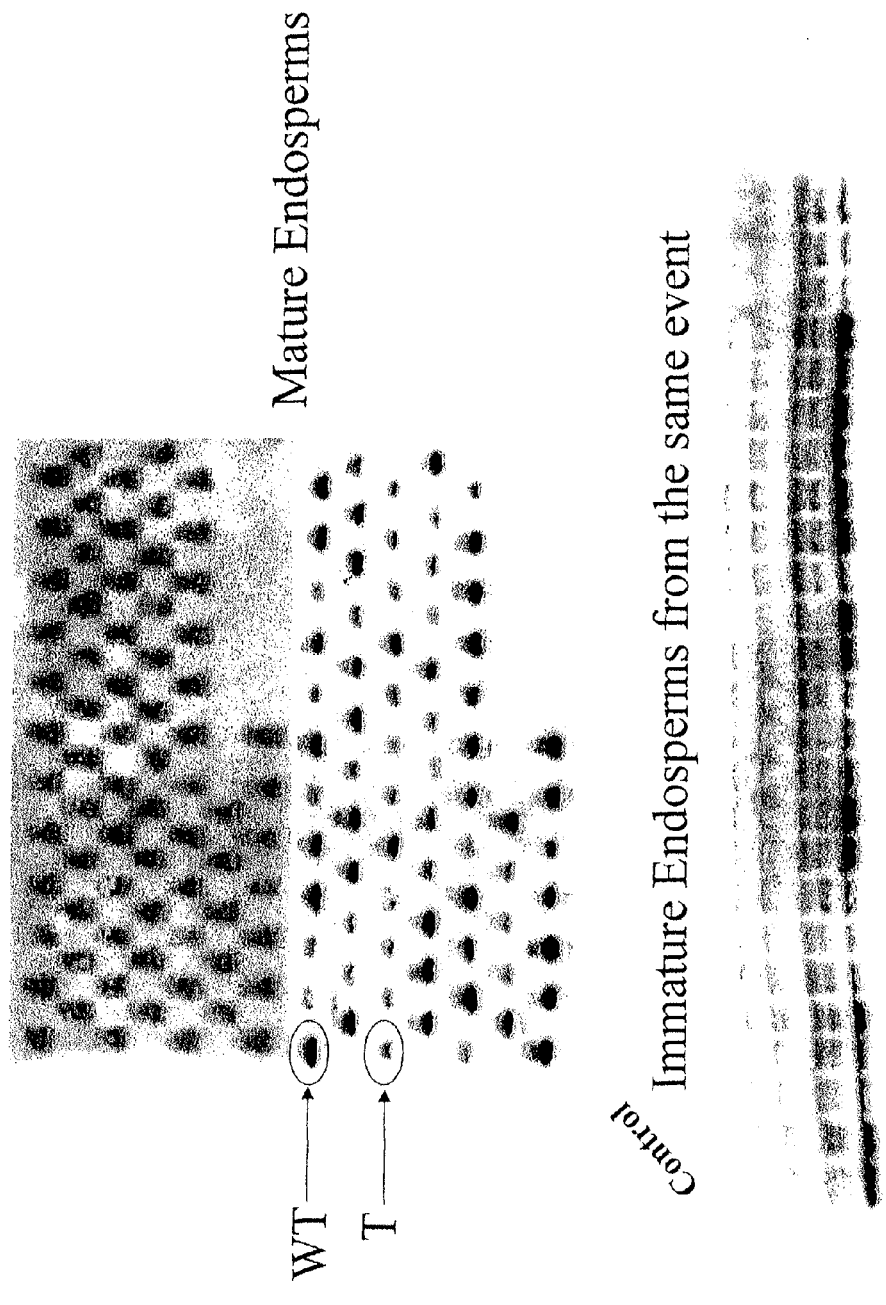
FIG. 3 depicts a total protein stain and Western blot of wild-type (WT) maize mature endosperm and transgenic (T) maize mature endosperms comprising the RGP1 suppression construct. Mature kernels were obtained from the same transgenic event.
Figure 4:
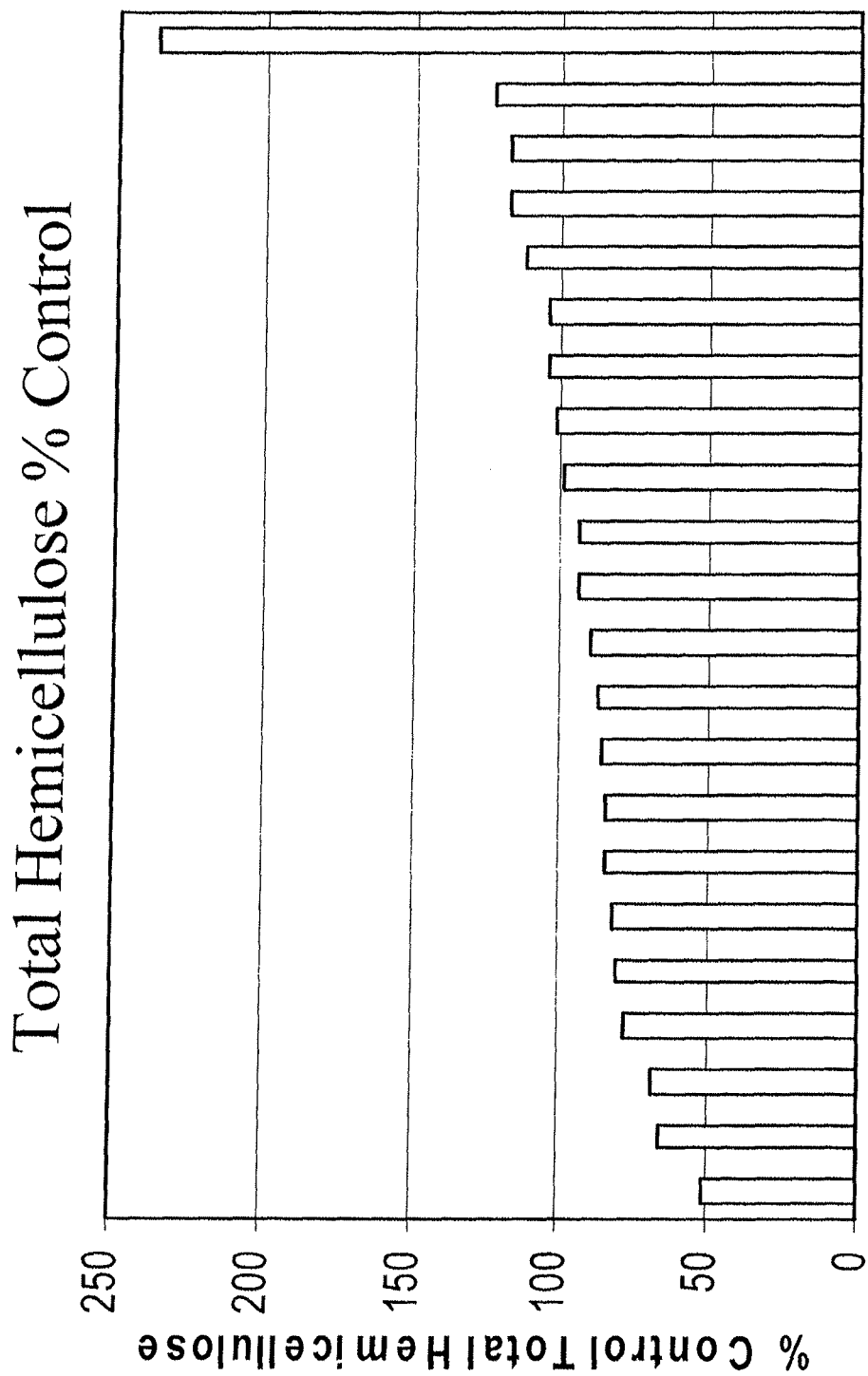
FIG. 4 depicts the total hemicellulose concentration (as a percent of control) for transgenic kernels comprising the RGP1 suppression construct. Those transgenic events yielding at least 3 wild-type and at least 3 transgenic kernels were selected for hemicellulose analysis. Twenty-two out of 36 transgenic events met these criteria. Kernels from the same ear were pooled into transgenic or wild-type for this analysis.
Figure 5:
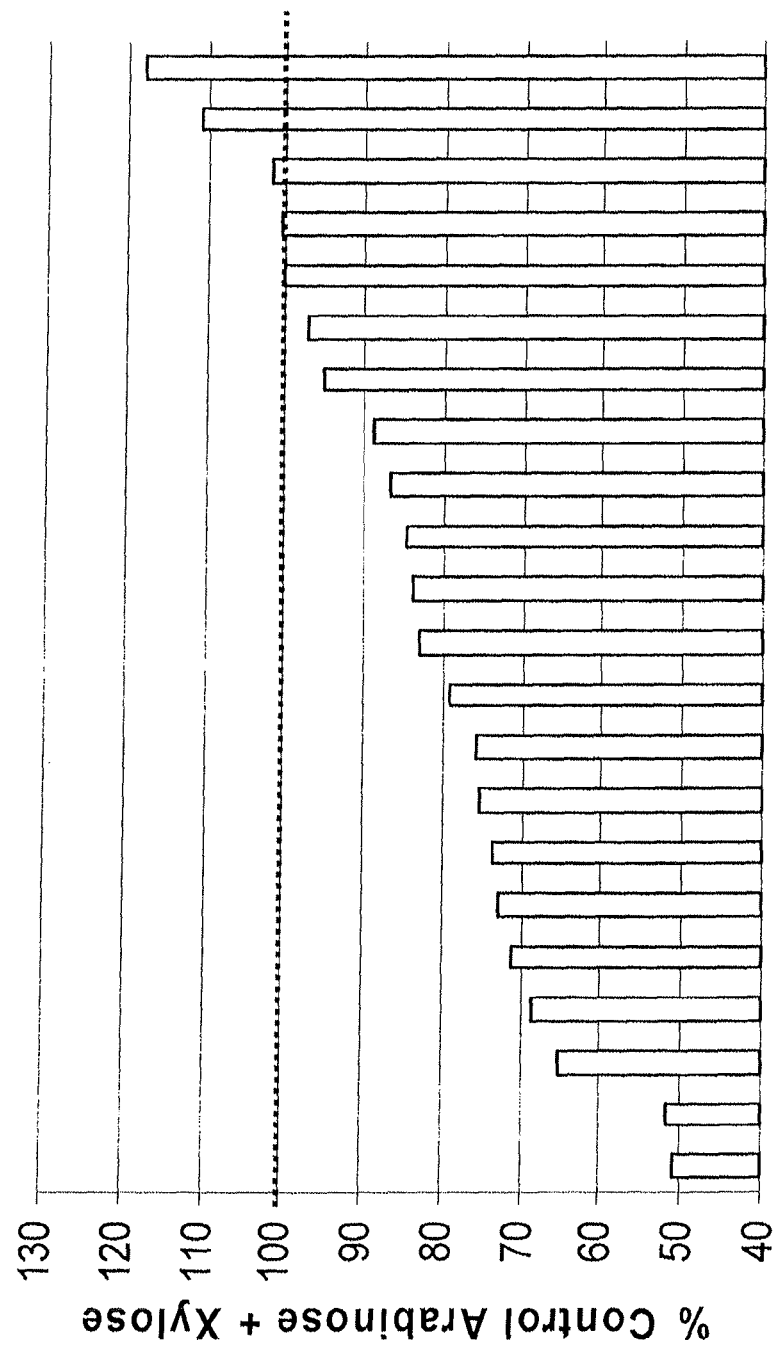
FIG. 5 depicts the total arabinose plus xylose concentration (as a percent of control) for transgenic kernels comprising the RGP-1 suppression construct. Analyses were as described for FIG. 4.
Figure 6:
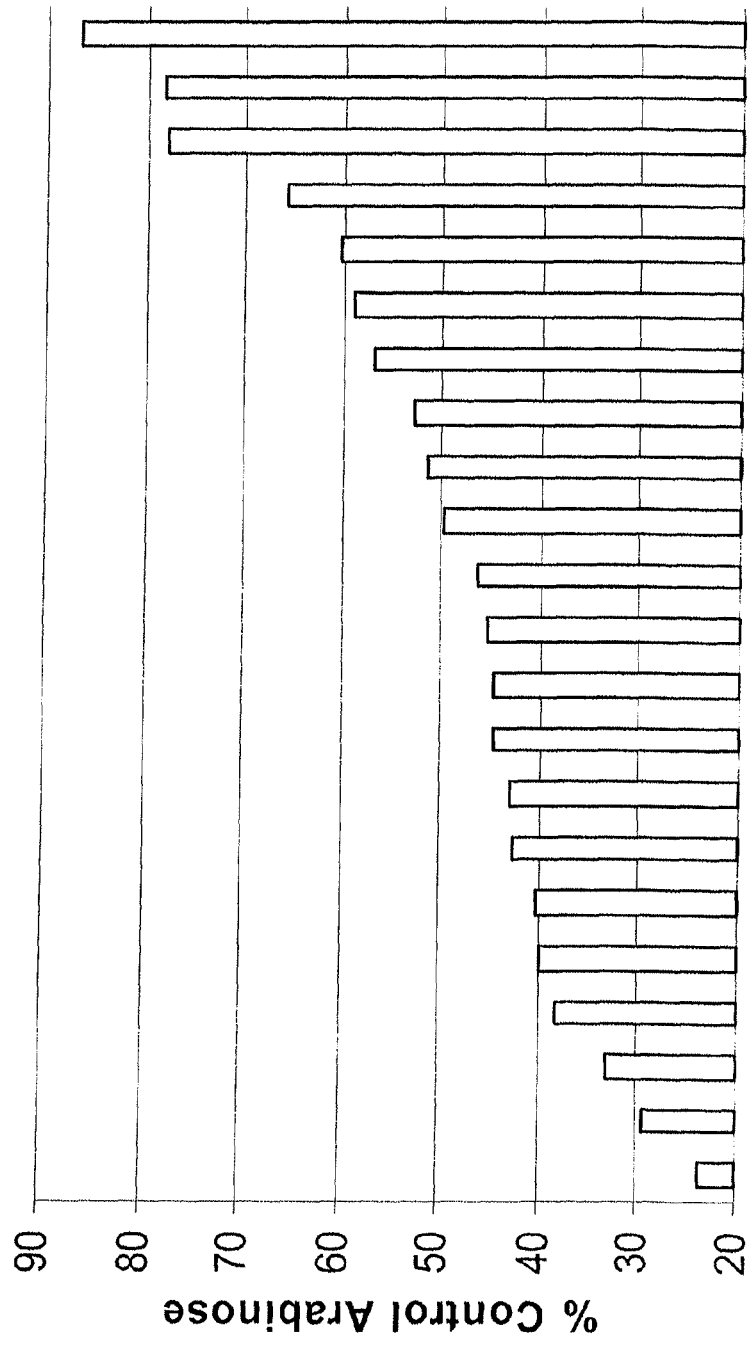
FIG. 6 depicts the total arabinose concentration (as a percent of control) for transgenic kernels comprising the RGP-1 suppression construct. Analyses were as described for FIG. 4.
Figure 7:
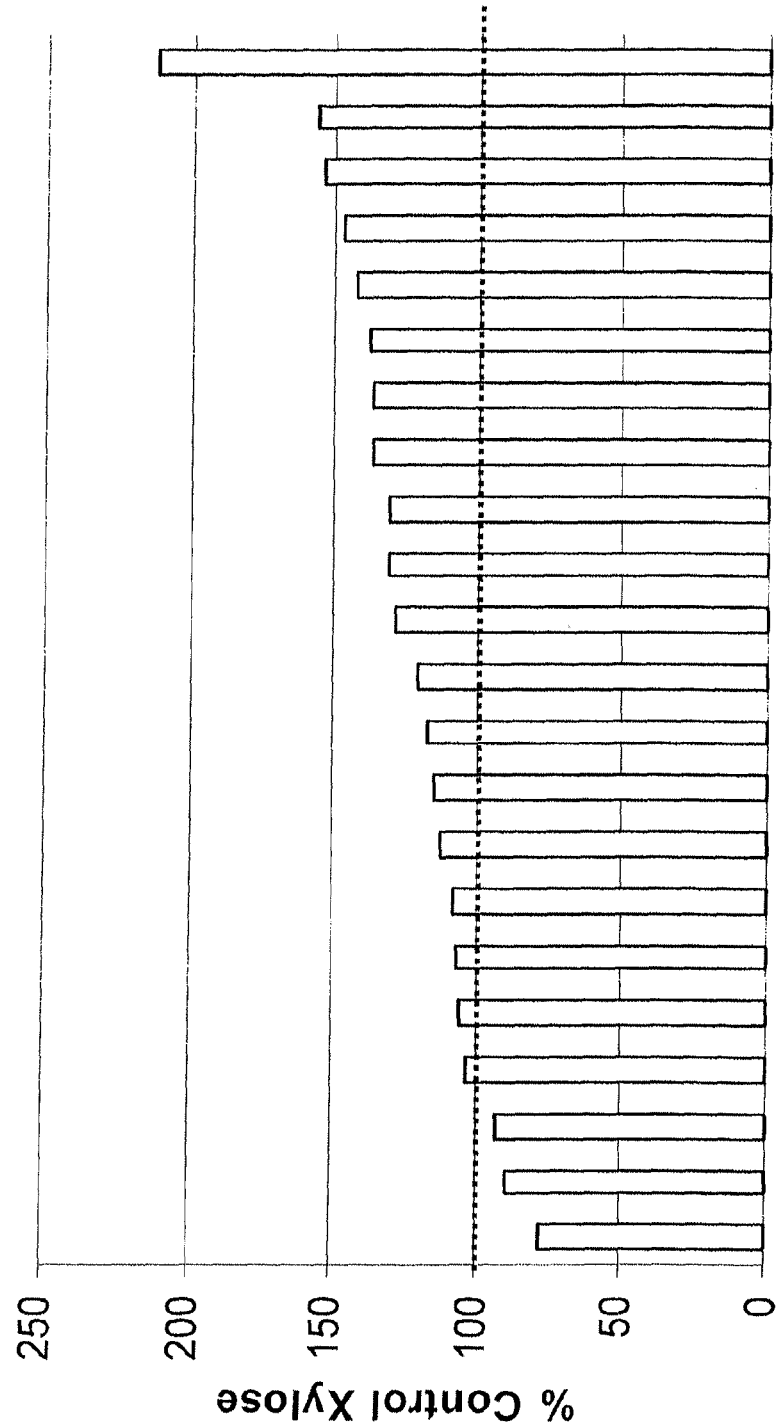
FIG. 7 depicts the total xylose concentration (as a percent of control) for transgenic kernels comprising the RGP-1 suppression construct. Analyses were as described for FIG. 4.
Figure 8:
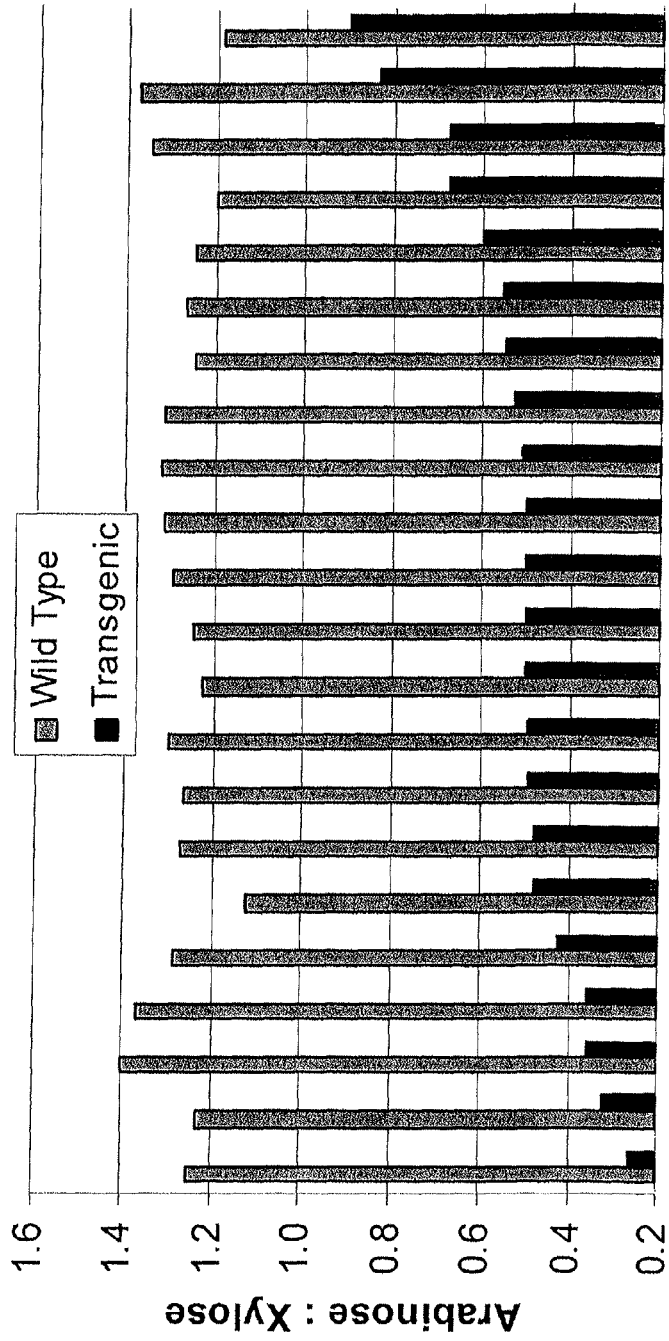
FIG. 8 depicts the ratio of arabinose to xylose for transgenic kernels comprising the RGP-1 suppression construct as compared to the corresponding ratio for wild-type kernels. Analyses were as described for FIG. 4.
Figure 9:
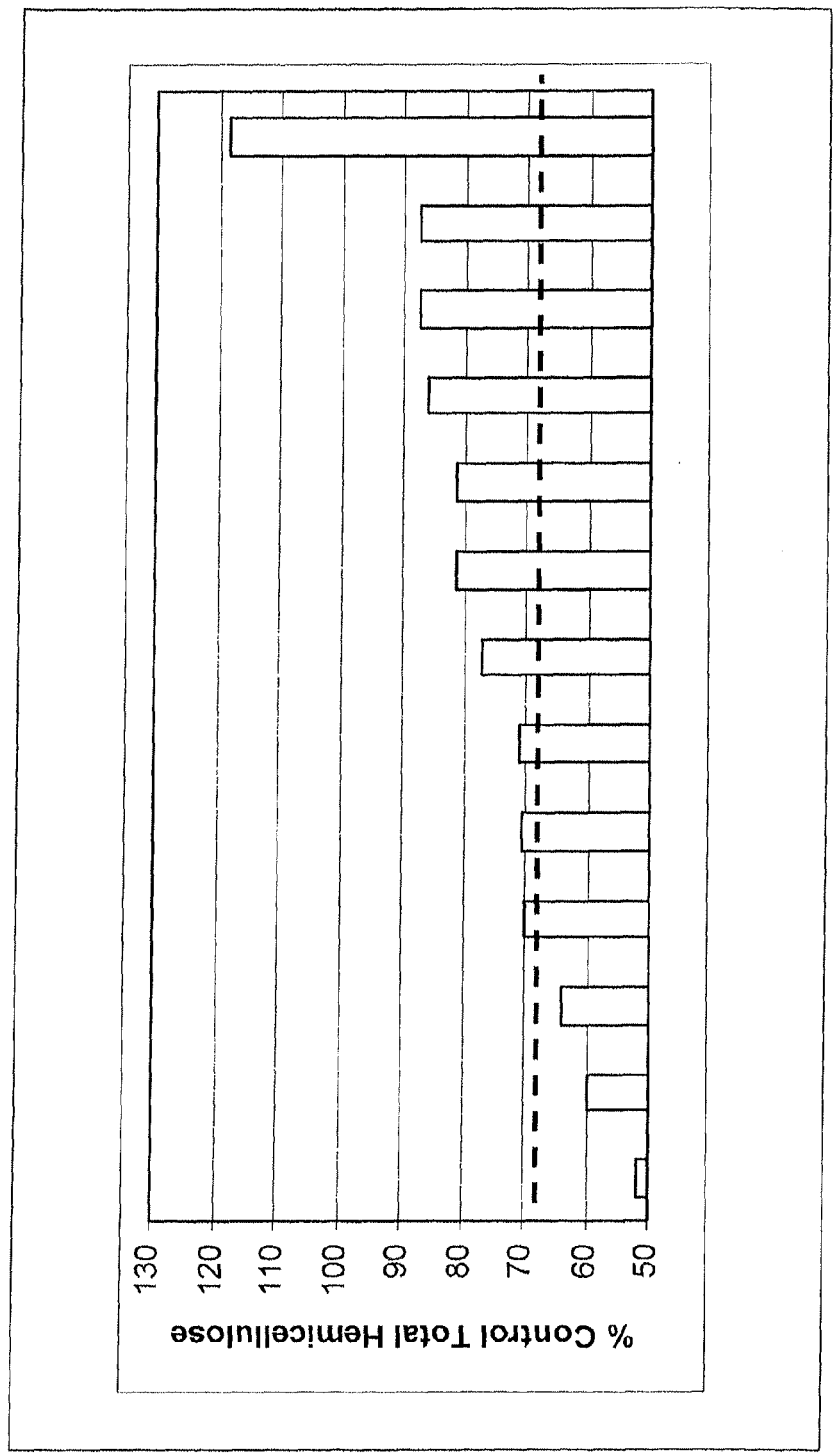
FIG. 9 depicts the total hemicellulose concentration (as a percent of control) for transgenic kernels comprising the RGP-1 suppression construct. Mature endosperm of 18 kernels from each of 13 transgenic events were rescreened for hemicellulose and individual sugar content. Kernels from the same ear were pooled into transgenic or wild-type for this analysis.
Figure 11:
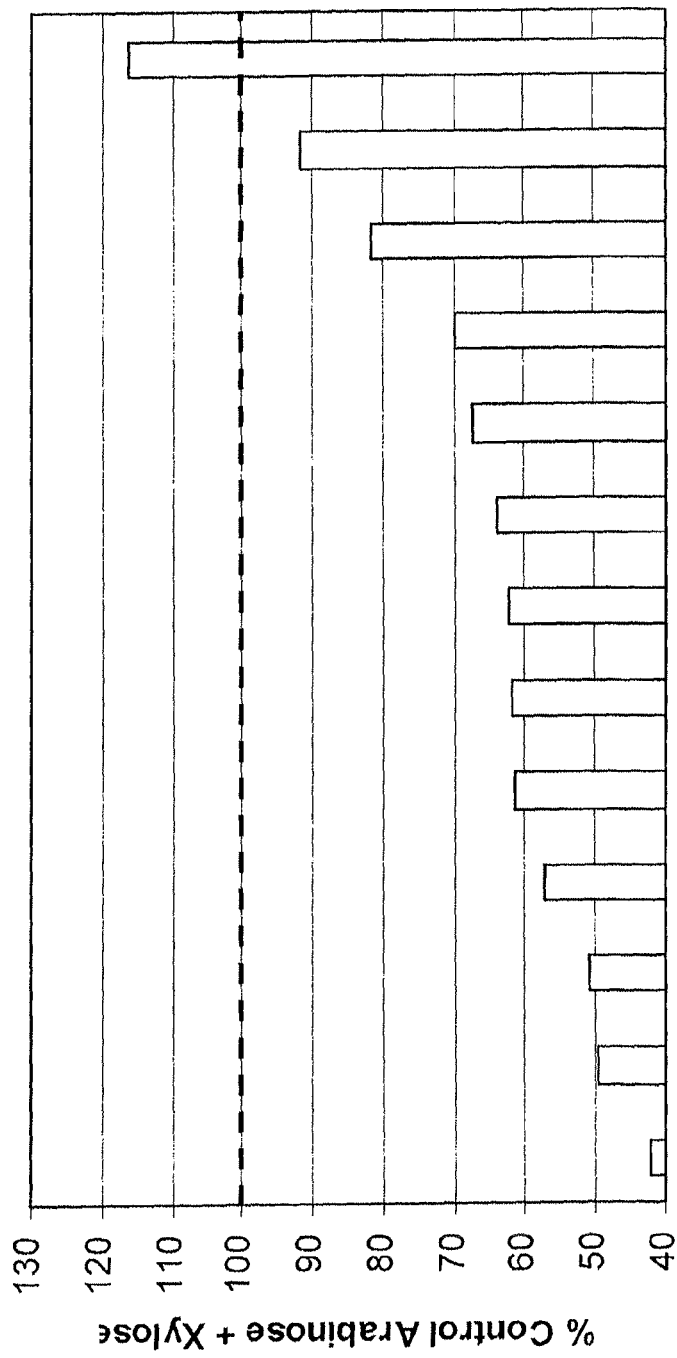
FIG. 11 depicts the total arabinose plus xylose concentration (as a percent of control) for transgenic kernels comprising the RGP-1 suppression construct. Analyses were as described for FIG. 9.
Figure 12:
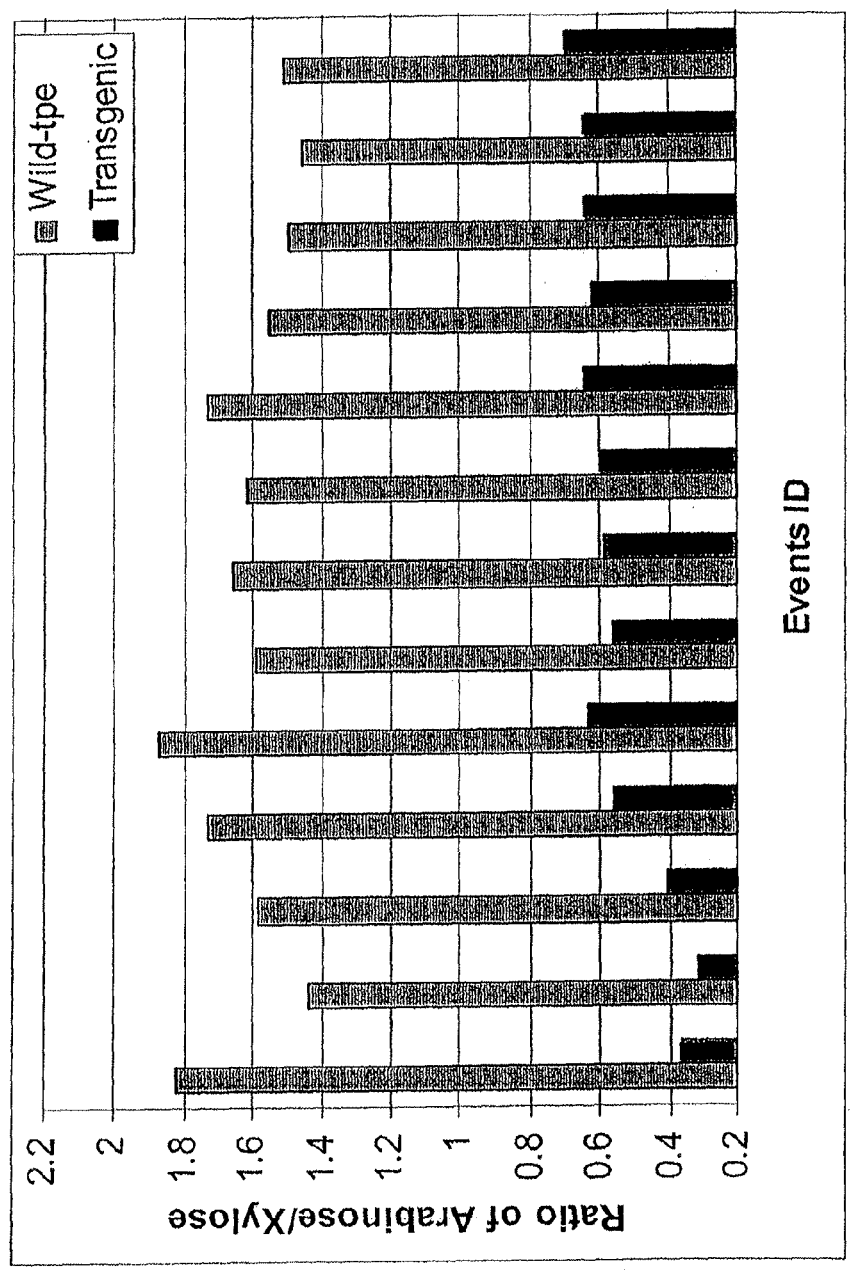
FIG. 12 depicts the ratio of arabinose to xylose for transgenic kernels comprising the RGP-1 suppression construct as compared to the corresponding ratio for wild-type kernels. Analyses were as described for FIG. 9.
Figure 13:
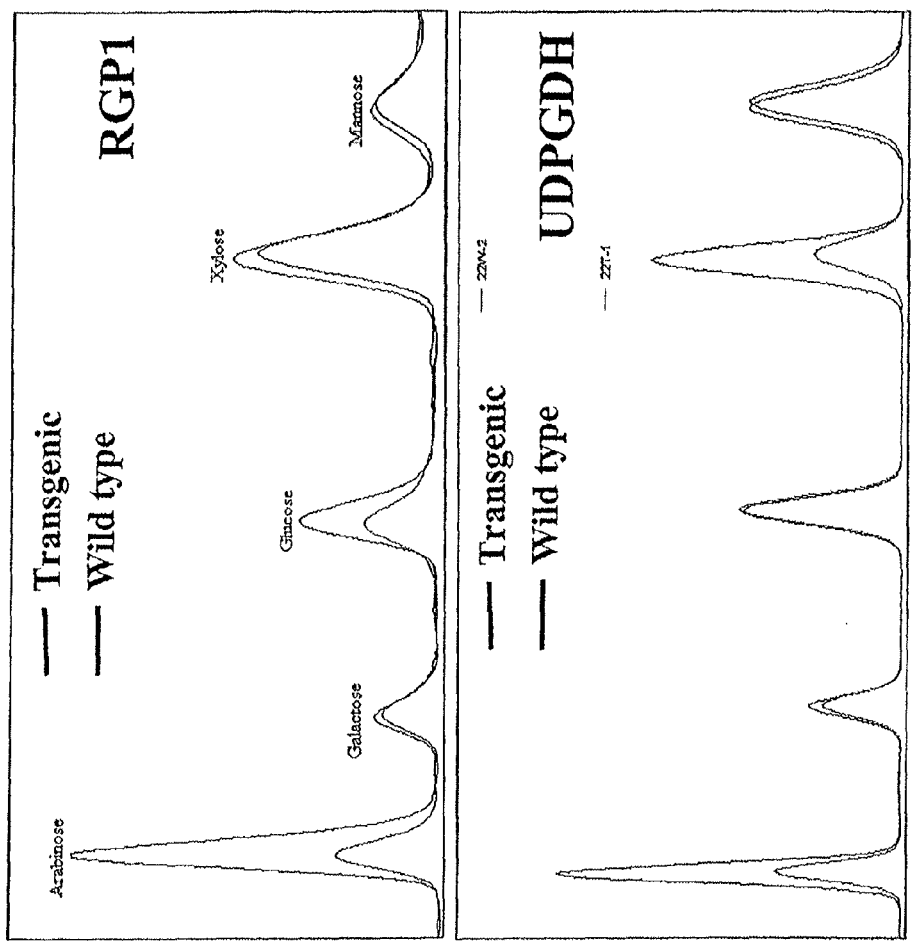
FIG. 13 depicts a chromatogram of sugar concentrations in transgenic kernels as compared to wild-type kernels for transgenic kernels comprising either an RGP-1 suppression construct (top) or a UDP-glucose suppression construct.

One-half of the embryo or endosperm was placed into a 96-well matrix snap rack (Matrix Technologies #4147). The tissue was ground in the Spex Certiprep GenoGrinder for two minutes at 1400 strokes/minute or until ground. One milliliter of extraction buffer (50 mM Tris, 100 mM DTT, 2% SDS) was added to each endosperm sample or 0.5 milliliter for embryo samples. The samples were ground again for 1 minute at 1400 strokes/minute in the GenoGrinder. The samples were heated at 100° C. for 5 minutes and centrifuged at 4,000 rpm for 10 minutes. Thirty microliters of supernatant was added to 10 µl of 4× E-PAGE loading dye Buffer 1 (Invitrogen catalog #EPBUF-01). Ten microliters was loaded onto Invitrogen's E-PAGE 96-well gel (catalog #EP096-06), and the gel was run for 14 minutes. For the Western blot, the proteins were transferred to PVDF membrane using semi-dry blotting apparatus for 1.5 hours at 0.8 mA/cm². The primary antibody used for the Western blot was a 1:5000 dilution of α-RGP1 antibody from pea. The secondary antibody was goat α-rabbit IgG (H+L)-HRP conjugated (BioRad #170-6515). The blot was developed using Amersham Biosciences ECL Western blotting detection reagents kit (RPN2106). Results of the Western blots and control Ponceau staining of the same blots are shown in FIG. 3.

Based on the results of the Western blots, events were screened for transformants. The results of the first screen are shown in Table 1.

TABLE 1

| Event | Knockdown | WT:T Ratio |
|---|---|---|
| 1 | fair/weak | 4:4 |
| 2 | fair | 3:5 |
| 3 | fair | 2:6 |
| 4 | fair | 4:4 |
| 5 | strong | 2:6 |
| 6 | fair/weak | 4:4 |
| 7 | strong | 3:5 |
| 8 | fair/strong | 4:4 |
| 9 | strong | 5:3 |
| 10 | fair/strong | 4:4 |
| 11 | fair/strong | 4:4 |
| 12 | fair | 4:4 |
| 13 | fair | 4:4 |
| 14 | strong | 5:3 |
| 15 | strong | 5:3 |

Sample Preparation for Analysis of Hemicellulose Sugars

The remaining ½ embryo or ½ endosperm was pooled into wild-type or transgenic for each event based on the Western blot results. The pooled endosperm or embryo was ground in the Gendogrinder into a powder. Fifty milligram samples were weighed out for hemicellulose analysis. Soluble sugars were removed by adding 1 ml 80% ethanol and a small stir bar to each 50-mg sample of ground tissue. The samples were vortexed and heated at 100° C. for one minute. Samples were centrifuged at 14,000 rpm for 10 minutes and the supernatant was discarded. To the pellet, 1 ml of acetone was added, and the samples were vortexed and centrifuged at 14,000 rpm for 10 minutes. The supernatant was discarded and the pellets were dried. The pellets were de-starched by adding 0.3 ml α-amylase solution (300 units/assay α-amylase in 50 mM MOPS (pH 7.0), 5 mM calcium chloride, 0.02% sodium-azide) and heated at 90-95° C. for 10 minutes with constant stirring using a magnetic stir plate. Then 0.2 ml amyloglucosidase (Boehringer Manheim from *Aspergillus niger* catalog #1202367) solution (20 U/assay amyloglucosidase in 285 mM Sodium-acetate pH 4.5 0.02% Sodium-azide) was added to each tube and incubated at 55° C. overnight. Absolute ethanol was added to each tube to a final concentration of 70%, the samples were vortexed and centrifuged at 14,000 rpm for 10 minutes. The pellet was washed two times with 1 ml 80% ethanol discarding the supernatant each time. The pellet was washed with 1 ml acetone and left to dry. To hydrolyze the hemicellulose sugars, 1 ml of 1 M sulfuric acid was added, and the samples were heated at 100° C. for 30 minutes. The samples were cooled on ice and spun at 14,000 rpm for 10 minutes. The resulting supernatant was used for hemicellulose sugar analysis.

The average control weight of transformed kernel was tabulated (see Table 2) and the sugar content assayed.

TABLE 2

| Event | WT:T Ratio | Average WT Kernel wt. (mg) | Average T Kernel wt. (mg) | % Control Avg. wt. |
|---|---|---|---|---|
| 1 | 9:9 | 160.02 | 149.94 | 93.70 |
| 3 | 8:10 | 350.72 | 346.82 | 98.89 |
| 4 | 7:11 | 236.89 | 234.76 | 99.10 |
| 5 | 13:5 | 311.38 | 312.46 | 100.35 |
| 7 | 9:9 | 284.33 | 244.79 | 86.09 |
| 8 | 5:13 | 293.37 | 266.27 | 90.76 |
| 9 | 6:12 | 266.45 | 258.14 | 96.88 |
| 10 | 10:8 | 290.57 | 284.67 | 97.97 |
| 11 | 7:11 | 295.63 | 301.14 | 101.86 |
| 12 | 3:13 | 253.72 | 273.88 | 107.95 |
| 13 | 6:9 | 278.83 | 278.81 | 99.99 |
| 14 | 4:13 | 273.75 | 249.15 | 91.01 |
| 15 | 12:2 | 320.81 | 331.36 | 103.29 |
| Total | | 278.19 | 271.70 | 97.67 |

Analysis of High Performance Anion Exchange Chromatography with Pulsed Amperometric Detection (HPAEC_PAD)

HPAEC was used for separation, identification, and quantitation of arabinose, galactose, glucose, xylose, and mannose. A Dionex DX500 high performance liquid chromatograph (HPLC) equipped with a GP40 or GP50 pump, ED40 electrochemical detector, pulsed amperometric detector (PAD), and AS3500 autosampler was used. Samples were submitted as extracts and filtered through 0.2 μm spin filters and then quantitatively transferred to 1.8 mL glass vials and diluted with water to a concentration that allows quantification from a standard curve. Samples were kept refrigerated at 4° C. Ten-microliter injections were introduced to a Dionex CarboPac PA1 guard (4×50 mm) and analytical column (4×250 mm). An auxiliary pump delivered 300 mM sodium hydroxide through a T-juncture immediately post column but before the PAD at a constant flow rate of ~0.2 mL/minute. A six-point standard curve with a range from 0.5 μg/mL to 100 μg/mL was used for quantitation. Initial eluent conditions for sugar separation consist of 100% water at a flow rate of 1 mL/minute. Sugars eluted in the order of arabinose, galactose, glucose, xylose, and mannose at approximately 9, 10.5, 13, 16, and 18 minutes respectively. At 20 minutes, a step gradient consisting of 30%—water, 50%—600 mM NaOH, and 20%—300 mM NaOH/500 mM NaOAC, was used to rid the column of contaminants. At 32 minutes, a step gradient was used to return to 100% water conditions and re-equilibrate the column to initial conditions. Total run time was 43 minutes.

The results of the sugar content assays are shown in FIGS. 4 through 13. The cumulative results demonstrate that interference with RGP1 using a suppression cassette expressing hpRNA targeting expression of RGP1 decreases arabinose concentration in the seed, but not xylose concentration in the seed.

Example 2

Maize Transformation

Immature maize embryos from greenhouse donor plants are bombarded with a plasmid containing the suppression cassette and the selectable marker gene PAT (Wohlleben et al. (1988) *Gene* 70:25-37), which confers resistance to the herbicide Bialaphos. Alternatively, the selectable marker gene is provided on a separate plasmid. Transformation is performed as follows.

The ears are husked and surface sterilized in 30% Clorox bleach plus 0.5% Micro detergent for 20 minutes, and rinsed two times with sterile water. The immature embryos are excised and placed embryo axis side down (scutellum side up), 25 embryos per plate, on 560Y medium for 4 hours and then aligned within the 2.5 cm target zone in preparation for bombardment.

A plasmid vector comprising the suppression cassette described above and the selectable marker gene PAT is made. This plasmid DNA plus plasmid DNA containing a PAT selectable marker is precipitated onto 1.1 μm (average diameter) tungsten pellets using a $CaCl_2$ precipitation procedure as follows: 100 μl prepared tungsten particles in water; 10 μl (1 μg) DNA in Tris EDTA buffer (1 μg total DNA); 100 μl 2.5 M $CaCl_2$; and, 10 μl 0.1 M spermidine.

Each reagent is added sequentially to the tungsten particle suspension, while maintained on the multitube vortexer. The final mixture is sonicated briefly and allowed to incubate under constant vortexing for 10 minutes. After the precipitation period, the tubes are centrifuged briefly, liquid removed, washed with 500 ml 100% ethanol, and centrifuged for 30 seconds. Again the liquid is removed, and 105 μl 100% ethanol is added to the final tungsten particle pellet. For particle gun bombardment, the tungsten/DNA particles are briefly sonicated and 10 μl spotted onto the center of each macrocarrier and allowed to dry about 2 minutes before bombardment.

The sample plates are bombarded at level #4 in particle gun #HE34-1 or #HE34-2. All samples receive a single shot at 650 PSI, with a total of ten aliquots taken from each tube of prepared particles/DNA.

Following bombardment, the embryos are kept on 560Y medium for 2 days, then transferred to 560R selection medium containing 3 mg/liter Bialaphos, and subcultured every 2 weeks. After approximately 10 weeks of selection, selection-resistant callus clones are transferred to 288J medium to initiate plant regeneration. Following somatic embryo maturation (2-4 weeks), well-developed somatic embryos are transferred to medium for germination and transferred to the lighted culture room. Approximately 7-10 days later, developing plantlets are transferred to 272V hormone-free medium in tubes for 7-10 days until plantlets are well established. Plants are then transferred to inserts in flats (equivalent to 2.5" pot) containing potting soil and grown for 1 week in a growth chamber, subsequently grown an additional 1-2 weeks in the greenhouse, then transferred to classic 600 pots (1.6 gallon) and grown to maturity. Mature kernels are collected and scored for expression of the desired phenotypic trait.

Bombardment medium (560Y) comprises 4.0 g/l N6 basal salts (SIGMA C-1416), 1.0 ml/l Eriksson's Vitamin Mix (1000×SIGMA-1511), 0.5 mg/l thiamine HCl, 120.0 g/l sucrose, 1.0 mg/l 2,4-D, and 2.88 g/l L-proline (brought to volume with D-I $H_2O$ following adjustment to pH 5.8 with KOH); 2.0 g/l Gelrite (added after bringing to volume with D-I $H_2O$); and 8.5 mg/l silver nitrate (added after sterilizing the medium and cooling to room temperature). Selection medium (560R) comprises 4.0 g/l N6 basal salts (SIGMA C-1416), 1.0 ml/l Eriksson's Vitamin Mix (1000×SIGMA-1511), 0.5 mg/l thiamine HCl, 30.0 g/l sucrose, and 2.0 mg/l 2,4-D (brought to volume with D-I $H_2O$ following adjustment to pH 5.8 with KOH); 3.0 g/l Gelrite (added after bringing to volume with D-I H₂O); and 0.85 mg/l silver nitrate and 3.0 mg/l bialaphos (both added after sterilizing the medium and cooling to room temperature).

Plant regeneration medium (288J) comprises 4.3 g/l MS salts (GIBCO 11117-074), 5.0 ml/l MS vitamins stock solution (0.100 g nicotinic acid, 0.02 g/l thiamine HCL, 0.10 g/l pyridoxine HCL, and 0.40 g/l glycine brought to volume with polished D-I H₂O) (Murashige and Skoog (1962) *Physiol. Plant.* 15:473), 100 mg/l myo-inositol, 0.5 mg/l zeatin, 60 g/l sucrose, and 1.0 ml/l of 0.1 mM abscisic acid (brought to volume with polished D-I H₂O after adjusting to pH 5.6); 3.0 g/l Gelrite (added after bringing to volume with D-I H₂O); and 1.0 mg/l indoleacetic acid and 3.0 mg/l bialaphos (added after sterilizing the medium and cooling to 60° C.). Hormone-free medium (272V) comprises 4.3 g/l MS salts (GIBCO 11117-074), 5.0 ml/l MS vitamins stock solution (0.100 g/l nicotinic acid, 0.02 g/l thiamine HCL, 0.10 g/l pyridoxine HCL, and 0.40 g/l glycine brought to volume with polished D-I H₂O), 0.1 g/l myo-inositol, and 40.0 g/l sucrose (brought to volume with polished D-I H₂O after adjusting pH to 5.6); and 6 g/l bacto-agar (added after bringing to volume with polished D-I H₂O), sterilized and cooled to 60° C.

Example 3

*Agrobacterium*-Mediated Transformation

For *Agrobacterium*-mediated transformation of maize with the suppression cassette, the method of Zhao is employed (U.S. Pat. No. 5,981,840, and PCT patent publication WO98/32326; the contents of which are hereby incorporated by reference). Briefly, immature embryos are isolated from maize and the embryos contacted with a suspension of *Agrobacterium*, where the bacteria are capable of transferring the suppression cassette of the invention to at least one cell of at least one of the immature embryos (step 1: the infection step). In this step the immature embryos are immersed in an *Agrobacterium* suspension for the initiation of inoculation. The embryos are co-cultured for a time with the *Agrobacterium* (step 2: the co-cultivation step). The immature embryos are cultured on solid medium following the infection step. Following this co-cultivation period an optional "resting" step is contemplated. In this resting step, the embryos are incubated in the presence of at least one antibiotic known to inhibit the growth of *Agrobacterium* without the addition of a selective agent for plant transformants (step 3: resting step). The immature embryos are cultured on solid medium with antibiotic, but without a selecting agent, for elimination of *Agrobacterium* and for a resting phase for the infected cells. Next, inoculated embryos are cultured on medium containing a selective agent and growing transformed callus is recovered (step 4: the selection step). The immature embryos are cultured on solid medium with a selective agent resulting in the selective growth of transformed cells. The callus is then regenerated into plants (step 5: the regeneration step), and calli grown on selective medium are cultured on solid medium to regenerate the plants.

Example 4

Soybean Embryo Transformation

Soybean embryos are bombarded with a plasmid containing the suppression cassette of the invention as follows. To induce somatic embryos, cotyledons, 3-5 mm in length dissected from surface-sterilized, immature seeds of the soybean cultivar A2872, are cultured in the light or dark at 26° C. on an appropriate agar medium for six to ten weeks. Somatic embryos producing secondary embryos are then excised and placed into a suitable liquid medium. After repeated selection for clusters of somatic embryos that multiplied as early, globular-staged embryos, the suspensions are maintained as described below.

Soybean embryogenic suspension cultures can be maintained in 35 ml liquid media on a rotary shaker, 150 rpm, at 26° C. with florescent lights on a 16:8 hour day/night schedule. Cultures are subcultured every two weeks by inoculating approximately 35 mg of tissue into 35 ml of liquid medium.

Soybean embryogenic suspension cultures may then be transformed by the method of particle gun bombardment (Klein et al. (1987) *Nature (London)* 327:70-73, U.S. Pat. No. 4,945,050). A Du Pont Biolistic PDS1000/HE instrument (helium retrofit) can be used for these transformations.

A selectable marker gene that can be used to facilitate soybean transformation is a transgene composed of the 35S promoter from Cauliflower Mosaic Virus (Odell et al. (1985) *Nature* 313:810-812), the hygromycin phosphotransferase gene from plasmid pJR225 (from *E. coli*; Gritz et al. (1983) *Gene* 25:179-188), and the 3' region of the nopaline synthase gene from the T-DNA of the Ti plasmid of *Agrobacterium tumefaciens*. The expression cassette comprising the suppression cassette of the invention can be isolated as a restriction fragment. This fragment can then be inserted into a unique restriction site of the vector carrying the marker gene.

To 50 μl of a 60 mg/ml 1 μm gold particle suspension is added (in order): 5 μl DNA (1 μg/μl), 20 μl spermidine (0.1 M), and 50 μl CaCl₂ (2.5 M). The particle preparation is then agitated for three minutes, spun in a microfuge for 10 seconds and the supernatant removed. The DNA-coated particles are then washed once in 400 μl 70% ethanol and resuspended in 40 μl of anhydrous ethanol. The DNA/particle suspension can be sonicated three times for one second each. Five microliters of the DNA-coated gold particles are then loaded on each macro carrier disk.

Approximately 300-400 mg of a two-week-old suspension culture is placed in an empty 60×15 mm petri dish and the residual liquid removed from the tissue with a pipette. For each transformation experiment, approximately 5-10 plates of tissue are normally bombarded. Membrane rupture pressure is set at 1100 psi, and the chamber is evacuated to a vacuum of 28 inches mercury. The tissue is placed approximately 3.5 inches away from the retaining screen and bombarded three times. Following bombardment, the tissue can be divided in half and placed back into liquid and cultured as described above.

Five to seven days post bombardment, the liquid media may be exchanged with fresh media, and eleven to twelve days post-bombardment with fresh media containing 50 mg/ml hygromycin. This selective media can be refreshed weekly. Seven to eight weeks post-bombardment, green, transformed tissue may be observed growing from untransformed, necrotic embryogenic clusters. Isolated green tissue is removed and inoculated into individual flasks to generate new, clonally propagated, transformed embryogenic suspension cultures. Each new line may be treated as an independent transformation event. These suspensions can then be subcultured and maintained as clusters of immature embryos or regenerated into whole plants by maturation and germination of individual somatic embryos.

Example 5

Expression Profile of the Gbl2 Promoter

The most abundant proteins present in maize (*Zea mays* L.) embryos are saline soluble globulins. A Mr 45,000 globulin component, designated Glb2, is encoded by the Glb2 gene. A cDNA clone corresponding to Glb2 was used as a radiolabeled probe to examine the expression of Glb2 in developing embryos and other maize tissues. Glb2 transcripts accumulate during embryo development and are not detectable in germinating kernels. Glb2 transcripts are found only in the developing embryo, and not in endosperm, seedling, or unfertilized ears.

Figure 14:
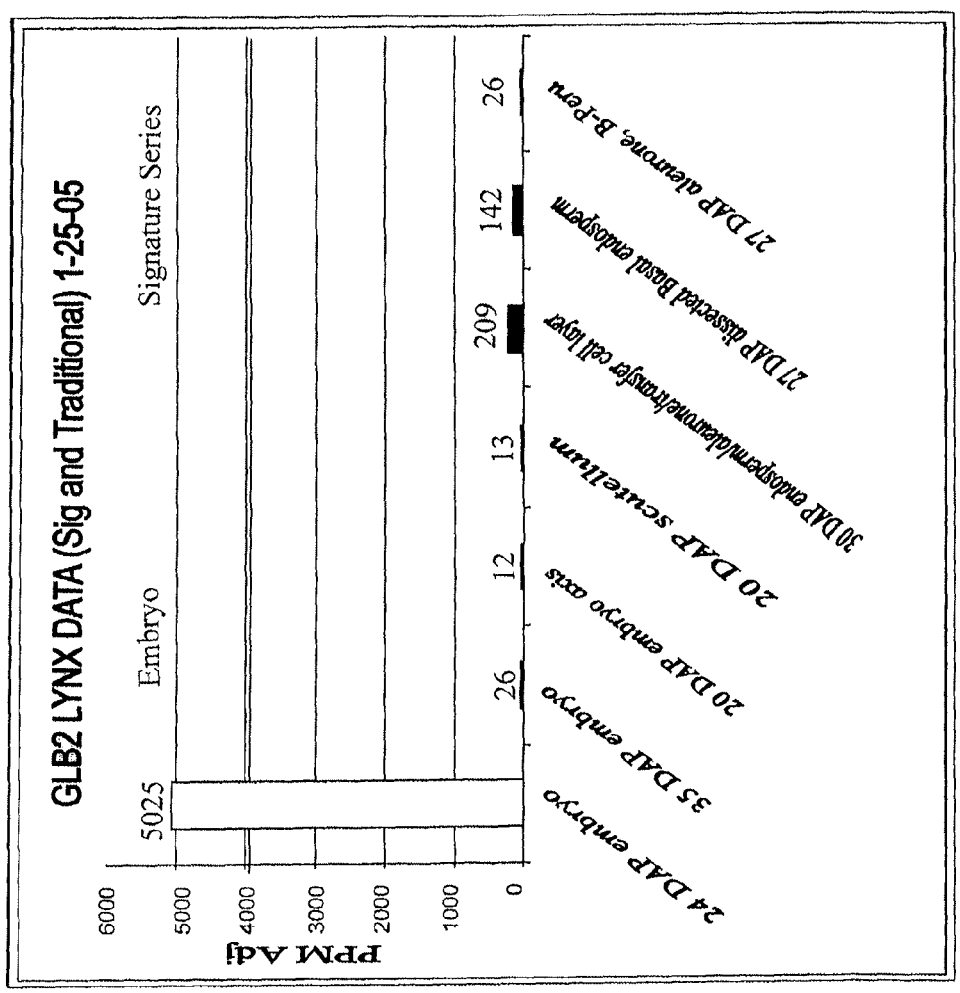
FIG. 14 shows LYNX data which demonstrates that the Glb2 promoter directs transcription between 20-24 DAP and is off by 35 DAP. Glb2 has virtually no signal from the aleurone which makes it very unique in the class of embryo promoters.

LYNX Data demonstrated that the GLB2 transcript is detected in very few libraries. It appears to come on between 20-24 DAP and off by 35 DAP. GLB2 has virtually no signal from the aleurone which makes it very unique in the class of embryo promoters. See, FIG. 14.

RT-PCR was also performed to determine the expression pattern of the Glb2 promoter. The GLB2 transcript is detected in whole kernel samples from 26-40 DAP. No signal was detected in vegetative samples. Data not shown.

And finally, Kernels were screened at 5 DAP intervals beginning at 10 DAP. Expression was observed first at 20 DAP. No expression was observed in leaf or pollen. Data not shown.

All publications and patent applications mentioned in the specification are indicative of the level of those skilled in the art to which this invention pertains. All publications and patent applications are herein incorporated by reference to the same extent as if each individual publication or patent application was specifically and individually indicated to be incorporated by reference.

Although the foregoing invention has been described in some detail by way of illustration and example for purposes of clarity of understanding, it will be obvious that certain changes and modifications may be practiced within the scope of the appended claims.

That which is claimed:

1. A DNA suppression cassette comprising a silencing element flanked by a first operably linked convergent promoter at one terminus of the silencing element and a second operably linked convergent promoter at the opposing terminus of the silencing element, wherein the first and the second convergent promoters have different expression profiles are capable of driving expression of the silencing element, said silencing element is transcribed as a hairpin RNA, and expression of said silencing element decreases the expression level of reversibly glycosylated polypeptide-1 (RGP1); wherein said silencing element comprises, in the following order, a first segment, a second segment, and a third segment, wherein
   i) said first segment comprises at least about 20 nucleotides of SEQ ID NO:2 and said first fragment comprising at least 90% sequence complementary to a target polynucleotide encoding RGP1;
   ii) ii) said second segment comprises a loop of sufficient length to allow the silencing element to be transcribed as a hairpin RNA; and,
   iii) iii) said third segment comprises at least about 20 nucleotides having at least 85% complementary to the first segment.

2. The DNA suppression cassette of claim 1, wherein said first and said second convergent promoters are active in a plant cell.

3. A vector comprising the DNA suppression cassette of claim 1.

4. A plant comprising the DNA suppression cassette of claim 2.

5. A transgenic seed from the the plant of claim 4, wherein the transgenic seed comprises the DNA suppression cassette.

6. A method for decreasing the expression level of reversibly glycosylated polypeptide-1 (RGP1) in a plant, said method comprising
   a) introducing into a plant cell a DNA suppression cassette of claim 1; and,
   b) expressing said silencing element from both the first and the second convergent promoters, and thereby decreasing the expression level of RGP1.

* * * * *